United States Patent
Bennett et al.

(10) Patent No.: US 6,624,149 B2
(45) Date of Patent: *Sep. 23, 2003

(54) METHOD FOR NUCLEIC ACID TRANSFECTION OF CELLS

(75) Inventors: Michael J. Bennett, El Sobrante, CA (US); Stephan S. Rothman, Berkeley, CA (US); Michael H. Nantz, Davis, CA (US)

(73) Assignee: Genteric, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/766,320

(22) Filed: Jan. 18, 2001

(65) Prior Publication Data

US 2001/0051610 A1 Dec. 13, 2001

Related U.S. Application Data

(63) Continuation-in-part of application No. 09/487,089, filed on Jan. 19, 2000, now Pat. No. 6,372,722.

(51) Int. Cl.⁷ .............................................. A61K 48/00
(52) U.S. Cl. .................. 514/44; 424/450; 435/320.1; 435/69.1; 435/325; 435/455; 435/458
(58) Field of Search .................. 514/44; 435/320.1, 435/455, 458, 325, 69.1; 424/450

(56) References Cited

U.S. PATENT DOCUMENTS

| | | | |
|---|---|---|---|
| 4,394,448 A | | 7/1983 | Szoka, Jr. et al. |
| 4,619,794 A | | 10/1986 | Hauser |
| 5,580,859 A | | 12/1996 | Felgner et al. |
| 5,693,531 A | | 12/1997 | Chiorini et al. |
| 5,703,055 A | | 12/1997 | Felgner et al. |
| 5,763,416 A | | 6/1998 | Bonadio et al. |
| 5,837,693 A | | 11/1998 | German et al. |
| 5,885,971 A | | 3/1999 | German et al. |
| 5,916,803 A | | 6/1999 | Sedlacek et al. |
| 5,929,226 A | | 7/1999 | Padmapriya et al. |
| 5,957,972 A | | 9/1999 | Williams et al. |
| 6,086,870 A | | 7/2000 | Welsh |
| 6,093,571 A | | 7/2000 | Watanabe et al. |
| 6,120,799 A | * | 9/2000 | McDonald et al. |
| 6,153,598 A | | 11/2000 | Filler et al. |

FOREIGN PATENT DOCUMENTS

| EP | WO 92/04916 | 4/1992 |
|---|---|---|

OTHER PUBLICATIONS

Bennett et al. Catonic lipid–mediated gene delivery to murine lung: correlation of lipid hydration with in vivo transfection activity pp. 4069–4078 1997.*

Reimer et al. lipsomal lipid and plasmid DNA delivery to B16/BL6 tumors after intraperitoneal administration of catonic liposome DNA aggregates vol. 289 No. 2 pp. 807–815 1999.*

Bennett et al., 1997, "Cationic lipid–mediated gene delivery to murine lung: correlation of lipid hydration with in vivo transfection activity," *J. Med. Chem.* 40:4069–4078.

Gerrard et al., 1993, "Towards gene therapy for haemophilia B using primary human keratinocytes," *Nat. Genet.* 3: 180–183.

Felgner and Ringold, 1989, "Cationic liposome–mediated transfection," *Nature* 337:387–388.

Kuklin et al., 1997, "Induction of mucosal immunity against herpes simplex virus by plasmid DNA immunization," *J. Virol.* 71:3138–3145.

Lee and Coffin, 1990, "Efficient autointegration of avian retrovirus DNA in vitro," *J. Virol.* 64:5958–5965.

McCluskie et al., 1999, "Route and method of delivery of DNA vaccine influence immune responses in mice and non–human primates," *Mol. Med.* 5:287–300.

Meyer et al., 1995, "Intratracheal gene delivery to the mouse airway: characterization of plasmid DNA expression and pharmacokinetics," *Gene Ther.* 2:450–460.

Morgan et al., 1987, "Expression of an exogenous growth hormone gene by transplantable human epidermal cells," *Science* 237:1476–1479.

Raz et al., 1994, "Intradermal gene immunization: the possible role of DNA uptake in the induction of cellular immunity to viruses." *Proc. Nat. Acad. Sci. U.S.A.* 91:9519–9523.

Reimer et al., 1999, "Liposomal lipid and plasmid DNA delivery to B16/BL6 tumors after intraperitoneal administration of cationic liposome DNA aggregates," *J. Pharmacol. Exp. Ther.* 289:807–15.

Rivera et al., 1999, "Long–term regulated expression of growth hormone in mice after intramuscular gene transfer," *Proc. Natl. Acad. Sci. U.S.A.* 96:8657–8662.

(List continued on next page.)

Primary Examiner—Dave T. Nguyen
(74) Attorney, Agent, or Firm—Townsend and Townsend and Crew LLP

(57) ABSTRACT

The present invention describes methods for introducing nucleic acids into a target cell using a transition metal enhancer. A mixture containing nucleic acid and a transition metal enhancer is exposed to cells. The nucleic acid is taken up into the interior of the cell with the aid of the transition metal enhancer. Since nucleic acids can encode a gene, the method can be used to replace a missing or defective gene in the cell. The method can also be used to deliver exogenous nucleic acids operatively coding for proteins that are secreted or released from target cells, thus resulting in a desired biological effect outside the cell. Alternatively, the methods of the present invention can be used to deliver exogenous nucleic acids into a target cell that are capable of regulating the expression of a predetermined endogenous gene. This can be accomplished by encoding the predetermined endogenous gene on the nucleic acid or by encoding the nucleic acid with a sequence that is the Watson-Crick complement of the mRNA corresponding to the endogenous gene.

51 Claims, 3 Drawing Sheets

OTHER PUBLICATIONS

Ulmer et al., 1993, "Heterologous protection against influenza by injection of DNA encoding a viral protein," *Science* 259:1745–1749.

Verma and Somia, 1997, "Gene therapy—promises, problems and prospects," *Nature* 389:239–242.

Wang et al., 1993, "Gene inoculation generates immune responses against human immunodeficiency virus type 1," *Proc. Nat. Acad. Sci. U.S.A.* 90:4156–4160.

Wang et al., 1995, "Direct gene delivery of human tissue kallikrein reduces blood pressure in spontaneously hypertensive rats," *J. Clin. Invest.* 95:1710–1716.

Watanabe et al., 1999, "Intradermal delivery of IL–12 naked DNA induces systemic NK cell activation and Th1 response in vivo that is independent of endogenous IL–12 production," *J. Immunol.* 163:1943–1950.

Wisner et al., 1997, "A Modular Lymphographic Magnetic Resonance Imaging Contrast Agent: Contrast Enhancement with DNA Tranfection Potential," *J. Med. Chem.* 40:3992–3996.

Yang et al., 1997, "Increased Expression of $G_s\alpha$ Enhances Activiation of The Adenylyl Cyclase Signal Traansduction Cascade," *Molecular Endocrinology*, vol. 11 No. 8, pp. 1053–1061.

Wolff et al., 1990, "Direct gene transfer into mouse muscle in vivo," *Science* 247:1465–1468.

Zauner et al., (1998) "Polylysine–based transfection systems utilizing receptor–mediate delivery," *Adv Drug Deliv Rev* 30:97–113.

Mahat et al., (1999) Peptide–based gene delivery, *Curr Opin Mol Ther* 1:226–243.

Garnet, M.C., (1999) "Gene–delivery systems using cationic polymers," *Crit Rev Ther Drug Carrier Syst* 16:147–207.

Boussif et al., (1995) "A versatile vector for gene and oligonucleotide transfer into cells in culture and in vivo: polyethylenimine," *Proc Natl Acad Sci USA* 92:7297–7301.

Wagner, E., (1999) "Application of membrane–active peptides for nonviral gene delivery," *Adv Drug Deliv Rev* 38:279–289.

Gad et al., (1982) "Polycation–induced fusion of negatively–charged vesicles," *Biochim Biophys Acta* 690:124–132.

Ohki et al., (1986) "Effects of cations and polyamines on the aggregation and fusion of phosphatidylserine membranes," *Biochim Biophys Acta* 861:177–186.

Hong et al., (1983) Polyamines. Biological modulators of membrane fusion, *Biochim Biophys Acta* 732:469–472.

Ohki, S., (1982) "A mechanism of divalent ion–induced phosphatidylserine membrane fusion," *Biochim Biophys Acta* 689:1–11.

Haberland et al., (1999) "Calcium ions as efficient cofactor of polycation–mediated gene transfer," *Biochim Biophys Acta* 1445:21–30.

Melino et al., (1999) Zn(2+) ions selectively induce antimicrobial salivary peptide histatin–5 to fuse negatively charged vesicles. Identification and characterization of a zinc–binding motif present in the functional domain, *Biochemistry* 38:9626–9633.

Glaser et al., (1999) "Structure analysis of a fusogenic peptide sequence from the sea urchin fertilization protein bindin," *Biochemistry* 38:2560–2569.

Ulrich et al., (1998) "Membrane fusion is induced by a distinct peptide sequence of the sea urchin fertilization protein bindin," *J Biol Chem* 273:16748–16755.

Ulrich et al., (1999) "Ultrastructural characterization of peptide–induced membrane fusion and peptide self–assembly in the lipid bilayer," *Biophys J* 77:829–841.

Binder et al., (2000) "The effects of Zn(2+) on the secondary structure of a histidine–rich fusogenic peptide and its interaction with lipid membranes," *Biochim Biophys Acta* 1468:345–358.

Midoux et al., (1998) "Membrane permeabilization and efficient gene transfer by a peptide containing several histidines," *Bioconjug Chem.* 9:260–267.

Midoux et al., (1999) "Efficient gene transfer by histidylated polylysine/pDNA complexes," *Bioconjug Chem.* 10:406–411.

Midoux et al., (1993) "Specific gene transfer mediated by lactosylated poly–L–lysine into hepatoma cells," *Nucleic Acids Res.* 21:871–878.

Kunzelmann et al., (1993) "An immortalized cystic fibrosis tracheal epithelial cell line homozygous for the delta F508 CFTR mutation," *Am J Respir Cell Mol Biol.* 8:522–529.

Li et al., (1997) "Delivery of a PCR amplified DNA fragment into cells: a model for using synthetic genes for gene therapy," *Gene Ther.* 4:449–454.

Chen, TR (1977) "In situ detection of mycoplasma contamination in cell cultures by fluorescent Hoechst 33258 stain," *Exp Cell Res* 104:255–262.

Struck et al., (1981) "Use of resonance energy transfer to monitor membrane fusion," *Biochemistry* 20:4093–4099.

Smith et al., (1985) "Measurement of protein using bicinchoninic acid," *Anal Biochem* 150:76–85.

Hill et al., (1988) "Protein determination using bicinchoninic acid in the presence of sulfhydryl reagents," *Anal Biochem* 170:203–208.

Mosmann T., (1983) "Rapid colorimetric assay for cellular growth and survival: application to proliferation and cyotoxicity assays," *J Immunol Methods* 65:55–63.

Horan et al., (1989) "Stable cell membrane labelling," *Nature* 340:167–168.

Midoux et al., (1987) "Quantitation of the binding uptake and degradation of fluoresceinylated neoglycoproteins by flow cytometry," *Cytometry* 8:327–334.

Bello et al., (2001) "Histidylated polylysine as DNA vector: elevation of the imidazole protonation and reduced cellular uptake without change to the polyfection efficiency of serum stabilized negative polyplexes," *Bioconjug Chem* 12:92–99.

Maxfield, F.R., (1982) "Weak bases and ionophores rapidly and reversibly raise the pH of endocytic vesicles in cultured mouse fibroblasts," *J Cell Biol* 95:676–681.

Yamashiro et al., (1983) "Acidification of endocytic vesicles by an ATP–dependent proton pump," *J Cell Biol* 97:929–934.

Vallee et al., (1993) "The biochemical basis of zinc physiology,"0 *Physiol Rev* 73:79–118

Atar, et al., (1995) "Excitation–transcription coupling mediated by zinc influx through voltage–dependent calcium channels," *J Biol Chem* 270:2473–2477.

Maret et al., (1999) "Inhibitory sites in enzymes: zinc removal and reactivation from thionein," *Proc Natl Acad Sci USA* 96:1936–1940.

Elferink, J.G., (1991) "Changes of plasma membrane permeability in neutrophils treated with polycations," *Inflammation* 15:103–115.

Oku et al., (1986) "The fusogenic effect of synthetic polycations on negatively charged lipid bilayers," *J Biochem* 100:935–944.

Wang et al., (1984) Polyhistidine mediates and acid–dependent fusion of negatively charged liposomes, Biochemistry, 23:4409–4416.

Lechardeur et al., (1999) "Metabolic instability of plasmid DNA in the cytosol: a potential barrier to gene transfer," *Gene Ther.* 6:482–497.

Goodbey et al., (1999) Poly(ethyleneimine) and its role in gene delivery, *J Control Release* 60:149–160.

Anderson, 1998, "Human Gene Therapy," *Nature* *392*(Supp):25–30.

Bennett et al., 1997, "Cationic lipid–mediated gene delivery to murine lung: correlation of lipid hydration with in vivo transfection activity," *J. Med. Chem. 40*:4069–4078.

Crystal, 1995, "Transfer of genes to humans: early lessons and obstacles to success," *Science 270*:404–410.

Mastrangelo et al., 1996, "Gene therapy for human cancer: An essay for clinicians," *Seminars in Oncology 23*(1):4–21.

Meng and El–Deiry, "Tumor suppressor genes as targets for cancer gene therapy," In: *Gene Therapy of Cancer*, Academic Press, 1999, pp. 3–20.

Filion et al., 1998, Major Limitations in the Use of Cationic Liposomes for DNA Delivery, *International Journal of Pharmaceutics 162*:159–170.

* cited by examiner

METHOD FOR NUCLEIC ACID TRANSFECTION OF CELLS

1. CROSS REFERENCE TO RELATED APPLICATIONS

This application is a continuation-in-part of application Ser. No. 09/487,089 filed Jan. 19, 2000, now U.S. Pat. No. 6,372,722.

2. BACKGROUND OF THE INVENTION

The advent of recombinant DNA technology and genetic engineering has led to numerous efforts to develop methods that facilitate the transfection of therapeutic and other nucleic acid-based agents to specific cells and tissues. Known techniques provide for the delivery of such agents, including a variety of genes that are carried in recombinant expression constructs. These constructs are capable of mediating expression of the genes once they arrive within a cell. Such developments have been critical to many forms of molecular medicine, specifically gene therapy, whereby a missing or defective gene can be replaced by an exogenous copy of the functional gene.

Typically, nucleic acids are large, highly polar molecules. As such, nucleic acids face the impermeable barrier of the cellular membrane in eukaryotes and prokaryotes. The cell membrane acts to limit or prevent the entry of the nucleic acid into the cell. The development of various gene delivery methods has paralleled currently known gene therapy protocols. While much progress has been made in increasing the efficiency of gene delivery into cells, limited nucleic acid uptake or transfection remains a hindrance to the development of efficient gene therapy techniques.

Common approaches for delivering a nucleic acid into a cell include ex vivo and in vivo strategies. In ex vivo gene therapy methods, the cells are removed from the host organism, such as a human, prior to experimental manipulation. These cells are then transfected with a nucleic acid in vitro using methods well known in the art. These genetically manipulated cells are then reintroduced into the host organism. Alternatively, in vivo gene therapy approaches do not require removal of the target cells from the host organism. Rather, the nucleic acid may be complexed with reagents, such as liposomes or retroviruses, and subsequently administered to target cells within the organism using known methods. See, e.g., Morgan et al., Science 237:1476, 1987; Gerrard et al., Nat. Genet. 3:180, 1993.

Several different methods for transfecting cells can be used for either ex vivo or in vivo gene therapy approaches. Known transfection methods may be classified according to the agent used to deliver a select nucleic acid into the target cell. These transfection agents include virus dependent, lipid dependent, peptide dependent, and direct transfection ("naked DNA") approaches. Other approaches used for transfection include calcium co-precipitation and electroporation.

Viral approaches use a genetically engineered virus to infect a host cell, thereby "transfecting" the cell with an exogenous nucleic acid. Among known viral vectors are recombinant viruses, of which examples have been disclosed, including poxviruses, herpesviruses, adenoviruses, and retroviruses. Such recombinants can carry heterologous genes under the control of promoters or enhancer elements, and are able to cause their expression in vector-infected host cells. Recombinant viruses of the vaccinia and other types are reviewed by Mackett et al., J. Virol. 49:3, 1994; also see Kotani et al., Hum. Gene Ther. 5:19, 1994.

However, viral transfection approaches carry a risk of mutagenicity due to possible viral integration into the cellular genome, or as a result of undesirable viral propagation. Many studies in vertebrate systems have established that insertion of retroviral DNA can result in inactivation or ectopic activation of cellular genes, thereby causing diseases. For a review, see Lee et al., J. Virol. 64:5958–5965, 1990. For example, one well known consequence of retroviral integration is activation of oncogenes. One study describes the activation of a human oncogene by insertion of HIV. Shiramizu et al., Cancer Res., 54:2069–2072, 1994. Viral vectors also are susceptible to interference from the host immune system.

Non-viral vectors, such as liposomes, may also be used as vehicles for nucleic acid delivery in gene therapy. In comparison to viral vectors, liposomes are safer, have higher capacity, are less toxic, can deliver a variety of nucleic acid-based molecules, and are relatively nonimmunogenic. See Felgner, P. L. and Ringold, G. M., Nature 337, 387–388, 1989. Among these vectors, cationic liposomes are the most studied due to their effectiveness in mediating mammalian cell transfection in vitro. One technique, known as lipofection, uses a lipoplex made of a nucleic acid and a cationic lipid that facilitates transfection into cells. The lipid/nucleic acid complex fuses or otherwise disrupts the plasma or endosomal membranes and transfers the nucleic acid into cells. Lipofection is typically more efficient in introducing DNA into cells than calcium phosphate transfection methods. Chang et al., Focus 10:66, 1988. However, some of the lipid complexes commonly used with lipofection techniques are cytotoxic or have undesirable non-specific interactions with charged serum components, blood cells, and the extracellular matrix. Furthermore, these liposome complexes can promote excessive non-specific tissue uptake.

One known protein dependent approach involves the use of polylysine mixed with a nucleic acid. The polysine/nucleic acid complex is then exposed to target cells for entry. See, e.g., Verma and Somia, Nature 389:239, 1997; Wolff et al., Science 247:1465, 1990. However, protein dependent approaches are disadvantageous because they are generally not effective and typically require chaotropic concentrations of polylysine.

"Naked" DNA transfection approaches involve methods where nucleic acids are administered directly in vivo. See U.S. Pat. No. 5,837,693 to German et al. Administration of the nucleic acid could be by injection into the interstitial space of tissues in organs, such as muscle or skin, introduction directly into the bloodstream, into desirable body cavities, or, alternatively, by inhalation. In these "Naked" DNA approaches, the nucleic acid is injected or otherwise contacted with the animal without any adjuvants, such as lipids or proteins, which typically results in only moderate levels of transfection, and the insufficient expression of the desired protein product. It has recently been reported that injection of free ("naked") plasmid DNA directly into body tissues, such as skeletal muscle or skin, can lead to protein expression, but also to the induction of cytotoxic T lymphocytes and antibodies against the encoded protein antigens contained in the plasmid. See Ulmer et al., Science, 259, 1993, 1745–1749; Wang et al., Proc. Nat. Acad. Sci. U.S.A. 90, 4157–4160, 1993; Raz et al., Proc. Nat. Acad. Sci. U.S.A. 91, 9519–9523, 1994.

Electroporation is another transfection method. See U.S. Pat. No. 4,394,448 to Szoka, Jr., et al. and U.S. Pat. No. 4,619,794 to Hauser. The application of brief, high-voltage electric pulses to a variety of animal and plant cells leads to the formation of nanometer-sized pores in the plasma membrane. DNA can enter directly into the cell cytoplasm either through these small pores or as a consequence of the redistribution of membrane components that accompanies closure of the pores. The use of electroporation as a tool to deliver DNA into cells has had limited success for in vivo applications.

A common disadvantage to known non-viral nucleic acid delivery techniques is that the amount of exogenous protein expression produced relative to the amount of exogenous nucleic acid administered remains too low for most diagnostic or therapeutic procedures. Low levels of protein expression are often a result of a low rate of transfection of the nucleic acid or the instability of the nucleic acid.

Despite numerous research efforts directed at finding efficient methods for nucleic acid delivery, most known techniques fail to result in sufficient cell transfection to achieve the desired protein expression. There is still a need to develop a nucleic acid delivery method that efficiently introduces recombinant expression constructs encoding useful genes into cells, while minimizing undesirable effects.

3. SUMMARY OF THE INVENTION

The present invention describes methods for introducing nucleic acids into a target cell using a transition metal enhancer. In accordance with the methods of the present invention, a mixture containing the nucleic acid and a transition metal enhancer is exposed to cells. The nucleic acid is then taken up into the interior of the cell with the aid of the transition metal enhancer. Since nucleic acids can encode a gene, the method can be used to replace a missing or defective gene in the cell. The method can also be used to deliver exogenous nucleic acids operatively coding for polypeptides that are secreted or released from target cells, thus resulting in a desired biological effect outside the cell. Alternatively, the methods can be used to deliver exogenous nucleic acids into a target cell that are capable of regulating the expression of a predetermined endogenous gene. This can be accomplished by encoding the predetermined endogenous gene on the nucleic acid or by encoding the nucleic acid with a sequence that is the Watson-Crick complement of the mRNA corresponding to the endogenous gene.

In particular, the present invention relates to a method for delivering a nucleic acid into a target cell by contacting a cell with a solution containing a nucleic acid and a transition metal enhancer. The cell may be derived from or contained within an organism or a primary cell culture. The nucleic acid sequence to be delivered is normally determined prior to use of the disclosed method. In some embodiments, a nucleic acid is delivered to a target cell by contacting a cell with a solution containing a nucleic acid, a transition metal enhancer and cationic lipid.

In one embodiment, the solution that facilitates intracellular delivery of therapeutically effective amounts of nucleic acid to target cells may be suitable for use with a variety of cell types including, but not limited to, those associated with the various secretory glands (e.g., mammary, thyroid, pancreas, stomach, and salivary glands), musculature connective tissue, bone, bladder, skin, liver, lung, kidney, the various reproductive organs such as testes, uterus and ovaries, nervous system, all other epithelial, endothelial, and mesodermal tissues.

In other embodiments, the transition metal enhancer is a complex, adduct, cluster or salt of a d-block element, a lanthanide, aluminum, and/or gallium. In yet other embodiments, the transition metal enhancer is a zinc, nickel, cobalt, copper, aluminum, or gallium complex.

The present invention provides a novel method for delivering a nucleic acid into a target cell. In accordance with the methods of the present invention, the nucleic acid and transition metal enhancer are exposed to cells. When the nucleic acid encodes a useful protein, the exposure may result in measurable expression of the protein. Such protein expression is useful in the practice of both diagnostic and therapeutic strategies.

4. BRIEF DESCRIPTION OF THE DRAWINGS

5. DETAILED DESCRIPTION OF THE INVENTION

Figure 1:
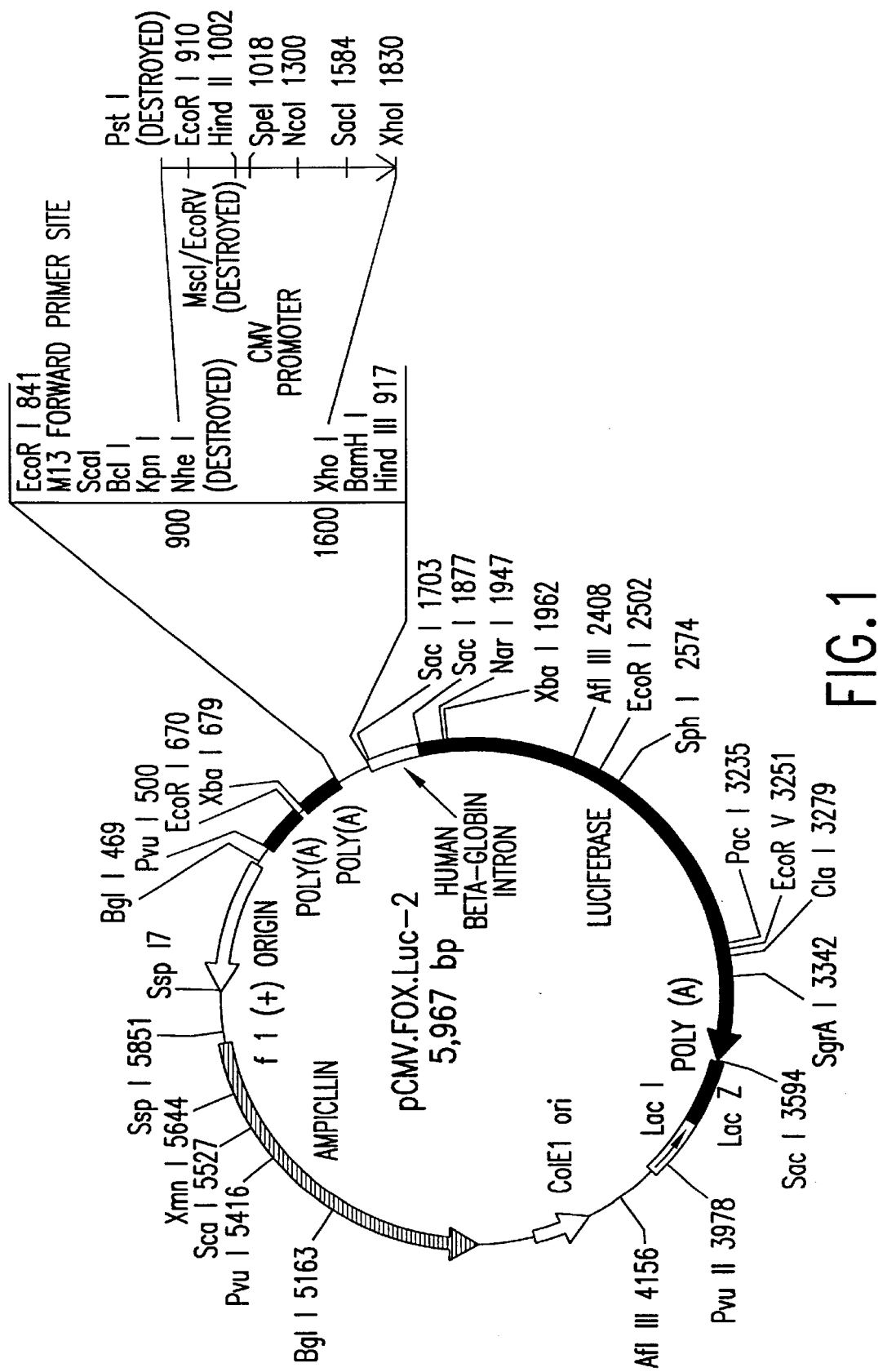
FIG. 1 is a schematic view of the recombinant plasmid pCMV.FOX.Luc-2, which encodes the luciferase gene.
Figure 2:
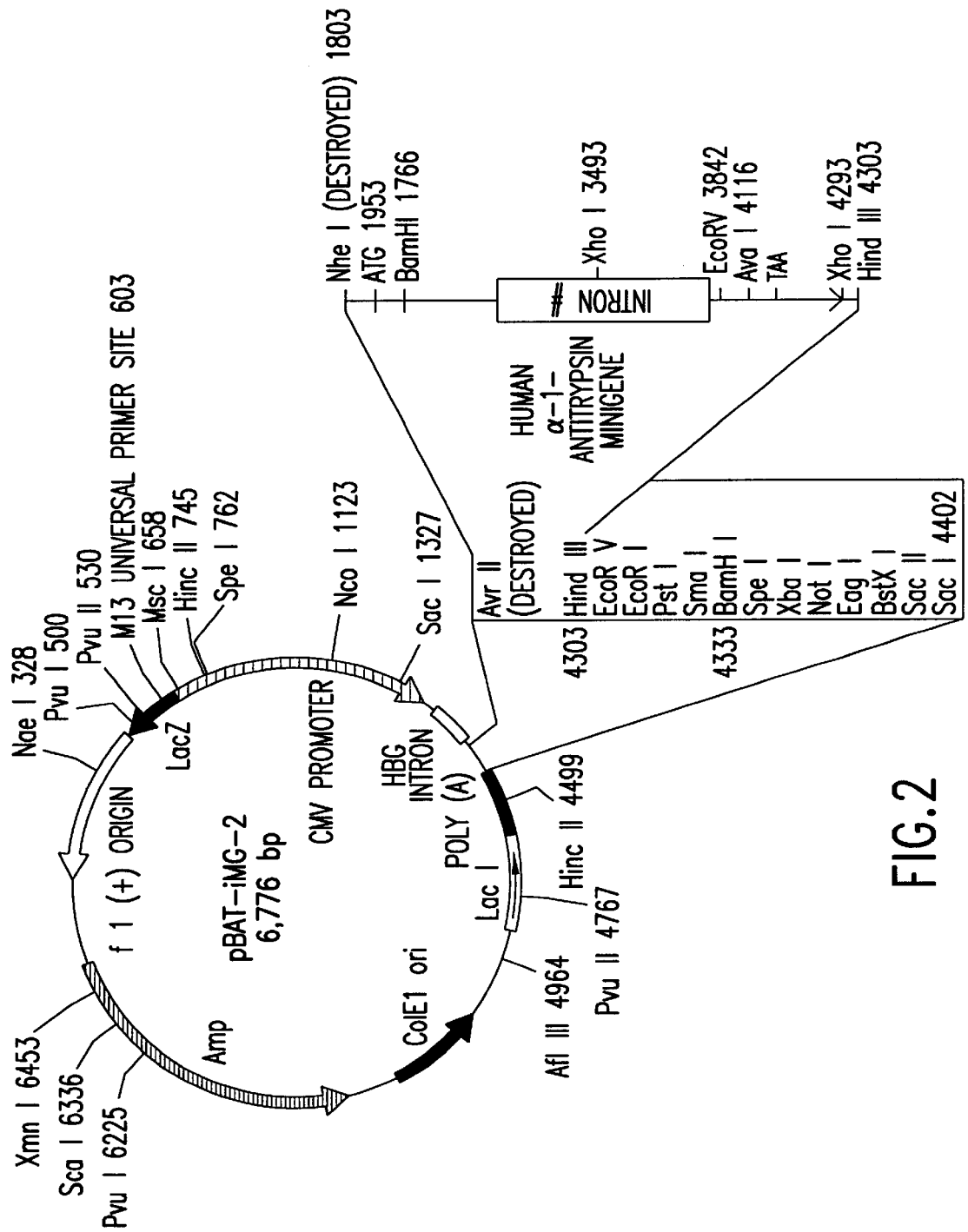
FIG. 2 is a schematic view of the recombinant plasmid pBAT-iMG-2, which encodes the human alpha-1 antitrypsin gene.

The present invention provides a method for transfection of a nucleic acid into a cell using a transition metal enhancer. In particular, a method for delivering a recombinant expression construct encoding a functional nucleic acid in the presence of a transition metal enhancer is disclosed. For the purposes of this invention, the term "recombinant expression construct" as used herein, is intended to mean a nucleic acid encoding a gene or fragment thereof, operably linked to a suitable control sequence capable of effecting the expression of the gene in a suitable host cell. Expressly intended to fall within the definition of a "gene" are embodiments comprising cDNA and genomic DNA encoding eukaryotic genes, as well as chimeric hybrids thereof. Also intended to fall within the scope of the recombinant expression constructs of the invention are fragments of such genes which, when expressed, may inhibit or suppress the function of an endogenous gene in a cell, including, antisense gene fragments.

The present invention describes a method for the delivery of an exogenous nucleic acid into a cell in the presence of a transition metal enhancer. The terms "delivery" or "deliver", as used in reference to nucleic acids, means that a nucleic acid and a cell are brought together such that the nucleic acid may contact and enter the cell. Nucleic acid delivery according to the methods of the present invention means that the nucleic acid comes into contact with a cell in the presence of a transition metal enhancer.

The entry of a nucleic acid into a cell using the methods of nucleic acid delivery of the present invention may take place in any way and preferably leads to an increase in the amount of the nucleic acid in the cell. Moreover, a nucleic acid delivered into a cell using the methods of the present invention is present in an active form within the cell, i.e., it is capable of being transcribed, or may be capable of hybridizing to other nucleic acids, or it is capable of being translated into a functional protein product.

Nucleic acids of any kind may be delivered into a cell, including, but not limited to, naturally occurring nucleic acids (e.g., genomic DNA, mRNA, tRNA, etc.), any synthetic nucleic acid, nucleic acids that have been modified, and nucleic acids that include one or more protecting groups. The nucleic acids may be delivered to the target cells using various in vivo, ex vivo or in vitro techniques.

In one embodiment, nucleic acids that can be used in accordance with the present invention include genomic or cDNA nucleic acids well known in the art. Typically, nucleic acid sequence information for a desired protein can be found in one of many public databases, such as, for example, GENBANK, EMBL, Swiss-Prot. Nucleic acid sequence information may also be found in journal publications. Thus, one of skill in the art has access to nucleic acid information for virtually all known genes having a published sequence. Therefore, in accordance with the present invention, one of skill in the art can either obtain the corresponding nucleic acid molecule directly from a public depository, or the institution or researcher that published the sequence.

In another embodiment, the cDNA encoding the desired protein product can then be used to make nucleic acid expression constructs and vectors as described herein. See, e.g., Vallette et al., 1989, Nucleic Acids Res., 17:723–733; and Yon and Fried, 1989, Nucleic Acids Res., 17:4895. Thus, virtually all known nucleic acids encoding a therapeutic nucleic acid sequence of interest are appropriate for use in the methods of the present invention.

Nucleic acid delivery according to the methods of the present invention discloses that a nucleic acid, a transition metal enhancer, and a target cell are brought together sequentially or collectively, as in a solution. In this way, the nucleic acid and the transition metal enhancer are allowed to contact each other prior to contact with the target cell. The mixing or bringing together of the nucleic acid, the transition metal enhancer and the target cell can be accomplished in any way known to the skilled person in the art.

In the methods of the present invention, nucleic acid/transition metal enhancer mixture can be formed by mixing an exogenous nucleic acid of interest with at least one transition metal enhancer. The nucleic acid/transition metal enhancer mixture is then administered to target cells. "Administration" may be defined as any route that will expose nucleic acids to target cells. For example, the solution may be administered intramuscularly, intratracheally, intraperitoneally, intradermally, intravenously, intraperineally, subcutaneously, intraductally, sublingually, by intranasal inhalation, intranasal instillation, intrarectally, intravaginally, ocularly, orally, intraductally into the ducts of the exocrine glands, and/or topical gene delivery. Examples of target cells that can receive the nucleic acid/transition metal enhancer mixture are an exocrine gland. An "exocrine gland" can be defined as a gland that releases a secretion external to or at the surface of an organ by means of a duct or a canal. Examples of exocrine glands are a salivary gland and the pancreas. Alternatively, target cells may be collected from the organism of interest and used to establish a primary culture using methods known in the art. The primary culture may then be contacted with the nucleic acid/transition metal enhancer mixture to allow physical uptake of the nucleic acid by cells of the primary culture. Then, the cells may be reintroduced to the target organism.

The present invention may be used in accordance with known in vivo and/or ex vivo gene therapy methods. For example, when the nucleic acid/transition metal enhancer mixture is used in ex vivo gene therapy techniques, target cells are collected from the organism of interest and then exposed directly to the nucleic acid/transition metal enhancer mixture. Alternatively, when the nucleic acid/transition metal enhancer solution is applied to various desirable in vivo approaches, the nucleic acid/transition metal enhancer mixture may be directly exposed to target cells following administration. For example, the target cells may be exposed to the gene by injecting the nucleic acid/transition metal enhancer solution into the interstitial space of tissues containing the target cells. More specifically, when the target cells of interest are muscle or skin cells, the nucleic acid/transition metal enhancer mixture may be injected into the interstitial space of muscle or skin. In addition to known applications in gene therapy, the methods of the present invention may be novelly applied as a general method in any application that requires physical uptake of nucleic acids into cells.

The application of the method of the present invention as applied to in vivo and ex vivo gene therapy approaches merely serves to illustrate one embodiment for the methods described by the present invention. In fact, target cells may be exposed to the nucleic acid/transition metal enhancer solution by any conventional technique beyond those typically used in in vivo and ex vivo gene therapy approaches.

Regardless of any method known to be in vivo, ex vivo, or any other method used to expose the nucleic acid/transition metal enhancer to target cells, sufficient exposure of the solution to the target cells will allow for the physical uptake of the nucleic acid into the target cells. In a preferred embodiment, the exogenous nucleic acid of interest codes for a polypeptide and is operably linked to a desired promoter that can cause transfection in the target cells. As defined herein, stable transfection occurs when the exogenous nucleic acid of interest is successfully incorporated into the genome of the target cell. Transient transfection is defined herein as any type of transfection that does not rely on the incorporation of the exogenous nucleic acid into the genome of the target cell.

In one embodiment, in which a portion of the exogenous nucleic acid of interest is transcribed, the transcribed mRNA is translated into a protein of interest. The translated protein may have a desired biological effect within the target cell, or alternatively, the targeted cell may secrete or release the translated protein and the protein may manifest a desired biological effect outside the cell.

5.1 Transition Metal Enhancers Useful For Nucleic Acid Delivery

5.1.1 General Description of Useful Transition Metal Enhancers

The transition metal enhancers of the present invention include transition metals, transition metal complexes, transition metal adducts, transition metal clusters, transition metal salts, and mixtures thereof. The transition metal enhancers also include any transition metal existing in chemical combination with a variety of other elements in a variety of ways. Specifically, transition metal atoms in the transition metal enhancers of the present invention may exist in one or more oxidation states, i.e., as a free ion or in bound form. In the transition metal enhancers of the present invention, transition metal atoms may themselves be directly bonded to ligands in complexes, loosely associated with other chemical species in adducts, or as ions in direct contact with other ions of opposite charge, "counter ions," or in salts. Complexes may have an overall charge and consequently be associated with counter-ions, to maintain neutrality.

The transition metal enhancers of the present invention include compounds having one or more transition metal atoms selected from the elements in Groups IIIB, IVB, VB, VIIB, VIIIB, IB, and IIB of the periodic table. This group of elements is defined herein as the d-block. See, e.g., Huheey, INORGANIC CHEMISTRY, Harper & Row, New York, 1983. The transition metal enhancers of the present invention also include those lanthanides and main group elements having chemical properties similar to transition metal complexes. As defined herein, lanthanides are the first row of the f-block of the periodic table and main group elements are those in groups IIIA, IVA, VA and VIIA of the periodic table, the first five groups of which is known to those of skill in the art as the p-block.

The transition metal enhancers of the present invention may be found in any complex form having any coordination number that is chemically possible, including, but not limited to a coordination number of 1, 2, 3, 4, 5, 6, 7, 8, or higher, and may further exhibit any geometric arrangement of ligands about the transition metal atom or ion including, but not limited to, tetrahedral, octahedral, square planar, trigonal bipyramidal, square based 10pyramidal, pentagonal bipyramidal and cubic. Furthermore, for any given shape, the transition metal enhancers of the present invention may exhibit any permitted stereochemistry, including, but not limited to cis and trans isomerism and may also undergo fluxional behavior whereby different isomers interchange faster than the timescale of observation. Furthermore, the transition metals enhancers of the present invention may be in any chemically possible oxidation state including, but not limited to, oxidation states zero, one, two, three or four and those that are formally negative. In addition, the present invention includes any isotope of any of the transition metals. The transition metal enhancers of the present invention may also include the transition metal atom or an ion free of any ligands.

5.1.2 Transition Metals

Any of the following metals may be combined with any inorganic or organic ligands, or mixtures of such ligands, to form the transition metal enhancer according to the methods of the present invention.

5.1.2.1 d-Block Elements

The transition metal enhancer of the present invention, include compounds containing scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, hafnium, tantalum, tungsten, rhenium, osmium, iridium, platinum, gold, mercury, or actinium. The transition metal enhancers of the present invention may also include compounds derived from members derived from the d-block commonly categorized as "trans-Actinide" elements, including rutherfordium, hahnium, and elements having an atomic number between 106 and 112.

5.1.2.2 Lanthanides

The transition metal enhancers of the present invention may also include lanthanide metals, complexes, adducts, clusters, salts, or enhancers thereof. As defined herein, the lanthanides include cerium, samarium, and gadolinium.

5.1.2.3 p-block Elements

The transition metal enhancers of the present invention include complexes, adducts, clusters, salts, and mixtures thereof, including a p-block element that has properties like transition metals such as copper. Therefore, the transition metal enhancers of the present invention include complexes, adducts, clusters, and/or salts that include aluminum, gallium, indium, tin, antimony, thallium, and lead.

5.1.3 Transition Metal Ligands

The ligands that may be used to complex or form adducts with the transition metals, and the similar members from the lanthanide series and p-block elements, to form a transition metal enhancer used according to the present invention, may be taken from the set of inorganic reagents as well as classes of compounds commonly found in organic chemistry.

5.1.3.1 Inorganic Ligands

The inorganic reagents that may be used to complex the elements comprising the transition metals to form the transition metal enhancers of the present invention include, but are not limited to, ammonia, cyanide anion, halides (including bromide, chloride, fluoride, and iodide), hydroxide, dinitrogen, carbon monoxide, dioxygen, oxychloride, hydrogen, water, and mixtures thereof.

5.1.3.2 Organic Ligands

The compounds that may be used to complex transition metals to form the transition metal enhancers of the present invention include, but are not limited to, alkyls, substituted alkyls, alkenyls, substituted alkenyls, cycloalkyls, substituted cycloalkyls, heterocycloalkyls, substituted heterocycloalkyls, aryls, alkaryls, heteroaryls, and alkheteroaryls.

As defined herein, alkyls are saturated branched, straight chain or cyclic hydrocarbon radicals. Typical alkyl groups include, but are not limited to, methyl, ethyl, propyl, isopropyl, cyclopropyl, butyl, isobutyl, t-butyl, cyclobutyl, pentyl, isopentyl, cyclopentyl, hexyl, cyclohexyl and the like. In a preferred embodiment, the alkyl groups of the present invention are $(C_1-C_{20})$ alkyls, more preferably $(C_1-C_{10})$ alkyls and most preferably $(C_1-C_5)$ alkyls.

As defined herein, substituted alkyls are alkyl radicals wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(NRR)=NR, —C(O)NROR, —C(NRR)=NOR, —NR—C(O)R, -tetrazol-5-yl, —NR—SO$_2$—R, —NR—C(O)—NRR, —NR—C(O)—OR, -halogen and -trihalomethyl where each R is independently —H, $(C_1-C_{20})$ alkyl, $(C_2-C_{20})$ alkenyl, $(C_2-C_{20})$ alkynyl, $(C_5-C_{20})$ aryl, and $(C_6-C_{26})$ alkaryl as defined herein.

As defined herein, alkenyls are unsaturated branched, straight chain or cyclic hydrocarbon radical having at least one carbon—carbon double bond. The radical may be in a cis or trans conformation about the double bond(s). Typical alkenyl groups include, but are not limited to, ethenyl, vinylidene, propenyl, propylidene, isopropenyl, isopropylidene, butenyl, butenylidene, isobutenyl, tert-butenyl, cyclobutenyl, pentenyl, isopentenyl, cyclopentenyl, hexenyl, cyclohexenyl and the like. In a preferred embodiment, the alkenyls of the present invention are $(C_2-C_{20})$ alkenyls, more preferably $(C_2-C_{10})$ alkenyls and most preferably $(C_2-C_5)$ alkenyls.

As defined herein, substituted alkenyls are alkenyl radicals wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(NRR)=NR, —C(O)NROR, —C(NRR)=NOR, —NR—C(O)R, -tetrazol-5-yl, —NR—SO$_2$—R, —NR—C(O)—NRR, —NR—C(O)—OR, -halogen and -trihalomethyl where each R is independently —H, $(C_1-C_8)$ alkyl, $(C_2-C_8)$ alkenyl, $(C_2-C_8)$ alkynyl, $(C_5-C_{20})$ aryl, and $(C_6-C_{26})$ alkaryl as defined herein.

As defined herein, cycloalkyls are cyclic or polycyclic saturated or unsaturated hydrocarbon radicals. Typical cycloalkyl groups include, but are not limited to, cyclopropanyl, cyclobutanyl, cyclopentanyl, cyclohexanyl and higher cycloalkyls, adamantyl, cubanyl, prismanyl and higher polycylicalkyls, and the like. In a preferred embodiment, the cycloalkyls of the present invention are $(C_3-C_{20})$ cycloalkyls.

As defined herein, substituted cycloalkyls are cycloalkyl radicals wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —(NRR)=NR, —C(O)NROR, —C(NRR)=NOR, —NR—C(O)R, -tetrazol-5-yl, —NR—SO$_2$—R, —NR—C(O)—NRR, —NR—C(O)—OR, -halogen and -trihalomethyl where each R is independently —H, $(C_1-C_8)$ alkyl, $(C_2-C_8)$ alkenyl, $(C_2-C_8)$ alkynyl, $(C_5-C_{20})$ aryl, and $(C_6-C_{26})$ alkaryl as defined herein.

As defined herein, heterocycloalkyls are cycloalkyl moieties wherein one of the ring carbon atoms is replaced with another atom such as N, P, O, S, As, Ge, Se, Si, Te, etc. Typical heterocycloalkyls include, but are not limited to, imidazolidyl, piperazyl, piperidyl, pyrazolidyl, pyrrolidyl, quinuclidyl, etc. In a preferred embodiment, the cycloheteroalkyl has between 5 and 10 members. Particularly preferred cycloheteroalkyls are morpholino, tetrahydrofuryl, and pyrrolidyl.

As defined herein, substituted heterocycloalkyls are cycloheteroalkyl radicals wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(NRR)=NR, —C(O)NROR, —C(NRR)=NOR, —NR—C(O)R, -tetrazol-5-yl, —NR—SO$_2$—R, —NR—C(O)—NRR, —NR—C(O)—OR, -halogen and -trihalomethyl where each R is independently —H, $(C_1-C_{20})$ alkyl, $(C_2-C_{20})$ alkenyl, $(C_2-C_{20})$ alkynyl, $(C_5-C_{20})$ aryl, $(C_6-C_{26})$ alkaryl, 5–20 membered heteroaryl, and 6–26 membered alk-heteroaryl as defined herein.

As defined herein, aryls are unsaturated cyclic hydrocarbon radicals having a conjugated π electron system. Typical aryl groups include, but are not limited to, penta-2,4-dienyl, phenyl, naphthyl, aceanthrylyl, acenaphthyl, anthracyl, azulenyl, chrysenyl, indacenyl, indanyl, ovalenyl, perylenyl, phenanthrenyl, phenalenyl, picenyl, pyrenyl, pyranthrenyl, rubicenyl and the like. In a preferred embodiment, the aryl group is $(C_5-C_{20})$ aryl, more preferably $(C_5-C_{10})$ aryl and most preferably phenyl.

As defined herein, alkaryls are straight-chain $(C_1-C_{20})$ alkyl, $(C_2-C_{20})$ alkenyl or $(C_2-C_{20})$ alkynyl groups wherein one of the hydrogen atoms bonded to the terminal carbon is replaced with an $(C_5-C_{20})$ aryl moiety. Alkaryls also refer to a branched-chain alkyl, alkenyl or alkynyl groups wherein one of the hydrogen atoms bonded to a terminal carbon is replaced with an aryl moiety. Typical alkaryl groups include, but are not limited to, benzyl, benzylidene, benzylidyne, benzenobenzyl, naphthalenobenzyl and the like. In a preferred embodiment, the alkaryl group is $(C_6-C_{26})$ alkaryl, i.e., the alkyl, alkenyl or alkynyl moiety of the alkaryl group is $(C_1-C_{20})$ and the aryl moiety is $(C_1-C_{20})$. In particularly preferred embodiments, the alkaryl group is $(C_6-C_{13})$, i.e., the alkyl, alkenyl or alkynyl moiety of the alkaryl group is $(C_1-C_3)$ and the aryl moiety is $(C_.-C_{10})$.

As defined herein, heteroaryls are aryl moieties wherein one or more carbon atoms have been replaced with another atom, such as N, P, O, S, As, Ge, Se, Si, Te, etc. Typical heteroaryl groups include, but are not limited to, acridarsine, acridine, arsanthridine, arsindole, arsindoline, benzodioxole, benzothiadiazole, carbazole, β-carboline, chromane, chromene, cinnoline, furan, imidazole, indazole, indole, isoindole, indolizine, isoarsindole, isoarsinoline, isobenzofuran, isochromane, isochromene, isoindole, isophosphoindole, isophosphinoline, isoquinoline, isothiazole, isoxazole, naphthyridine, perimidine, phenanthridine, phenanthroline, phenazine, phosphoindole, phosphinoline, phthalazine, piazthiole, pteridine, purine, pyran, pyrazine, pyrazole, pyridazine, pyridine, pyrimidine, pyrrole, pyrrolizine, quinazoline, quinoline, quinolizine, quinoxaline, selenophene, tellurophene, thiazopyrrolizine, thiophene and xanthene.

As defined herein, alk-heteroaryls are straight-chain alkyl, alkenyl or alkynyl groups where one of the hydrogen atoms bonded to a terminal carbon atom is replaced with a heteroaryl moiety. In a preferred embodiment, the alk-heteroaryl group is a 6–26 membered alk-heteroaryl, i.e., the alkyl, alkenyl or alkynyl moiety of the alk-heteroaryl is $(C_1-C_6)$ and the heteroaryl moiety is a 5–20-membered heteroaryl. In particularly preferred embodiments, the alk-heteroaryl has between 6 and 13 members, i.e., the alkyl, alkenyl or alkynyl moiety is $(C_1-C_3)$ and the heteroaryl moiety is a 5–10 membered heteroaryl.

Preferred organic ligands of the present invention are alkynes, such as acetylene and its derivatives, acetates, acetylacetonates, benzoates, ethylenebis(dithiocarbamates), butadiene, butylates, carboxylates (including formates, butanoates, propionates, pentanoates, hexanoates, octanoates, dodecanoates and decanoates), citrates, cyanoalkyls, alkylhalides, dimethylglyoximes, gluconates, glycinates, lactates, alkyl groups (including methyl, ethyl, propyl, iso-propyl, butyl, t-butyl), alkoxides (including, methoxide, ethoxide, oleates, oxalates, palmitates, phenoxides, phenolsulfonates, p-phenolsulfonates, propylene-bis(dithiocarbamate), salicylates, stearates, tartrates, alkylamines, alkenes (including ethylene, propene, butene), benzene and substituted benzenes, cyclobutadiene, cyclopentadiene, pyridine, cycloheptatriene, cyclo-octatetraene and the allyl group.

5.1.3.3 Adducts

Certain groups may act as counter-ions to the transition metals and their complexes or form adducts with them in order to form the transition metal enhancers according to the methods of the present invention. Such moieties include, but are not limited to, acetoarsenites, antimonides, arsenates, arsenides, arsenites, borates, carbonates, chromates, chromites, cyanides, cyanates, isocyanates, peroxides, hexafluorosulphates, hydrophosphites, hypophosphites, hydrosulfites, fluoroborates, ferrocyanides, meta-arsenites, metaborates, metaphosphates, nitrates, nitrate hexahydrates, nitrides, nitrites, ortho-arsenates, perchlorates, perchlorate hexahydrates, permanganates, phosphates, phosphides, phosphites, pyrophosphates, selenates, selenides, silicates, stannates, sulfates, sulfides, sulfites, thiocyanates, titanates, tungstates, and composite salts comprising one or more of the above.

5.1.4 Illustrative Transition Metal Enhancers

The transition metal enhancers that may be used according to the methods of the present invention include, but are not limited to, cobaltous nitrate, cobaltous oxide, cobaltic oxide, cobalt nitrite, cobaltic phosphate, cobaltous chloride, cobaltic chloride, cobaltous carbonate, chromous acetate, chromic acetate, chromic bromide, chromous chloride, chromic fluoride, chromous oxide, chromium dioxide, chromic oxide, chromic sulfite, chromous sulfate heptahydrate, chromic sulfate, chromic formate, chromic hexanoate, chromium oxychloride, chromic phosphite, cuprous oxide, cupric oxide, cupric chloride, cuprous acetate, cuprous oxide, cuprous chloride, cupric acetate, cupric bromide, cupric chloride, cupric iodide, cupric oxide, cupric sulfate and cupric sulfide, cupric propionate, cupric acetate, cupric metaborate, cupric benzoate, cupric formate, cupric dodecanoate, cupric nitrite; cupric oxychloride, cupric palmitate, cupric salicylate, manganese iodide, mangnese sulfate, manganous acetate, manganous benzoate, manganous carbonate, manganese chloride, manganese bromide, manganese dichloride, manganese trichloride, manganous citrate, manganous formate, manganous nitrate, manganous oxalate, manganese monooxide, manganese dioxide, manganese trioxide, manganese heptoxide, manganic phosphate, manganous pyrophosphate, manganic metaphosphate, manganous hypophosphite, manganous valerate, ferrous acetate, ferric benzoate, ferrous bromide, ferrous carbonate, ferric formate, ferrous lactate, ferrous nitrate, ferrous oxide, ferric oxide, ferric acetate, ferric hypophosphite, ferric sulfate, ferrous sulfite, ferric hydrosulfite, ferrous bromide, ferric bromide, ferrous chloride, ferric chloride, ferrous iodide, ferric iodide, nickel acetylacetonate, nickel bromide, nickel carbonate, nickel chloride, nickel cyanide, nickel dibromide, nickel dichloride, nickel dioleate, nickel fluoride, nickel fluoroborate, nickel hydroxide, nickel methylate, nickel nitrate, nickel nitrate hexahydrate, nickel oxide, nickel stearate, nickel sulfate, nickel sulfite, nickel thallate, or nickel salts of other organic acids such as ricinoleic acid, cobalt chloride, cobalt fluoride, cobalt nitrate, cobalt sulfate, cobalt octoate, cobalt fluoroborate, cobalt stearate, cobalt oxide, cobalt hydroxide, cobaltous bromide, cobaltous chloride, cobalt butylate, cobaltous nitrate hexahydrate, zinc chloride, zinc acetate, zinc bromide, zinc carbonate, zinc citrate, zinc fluoride, zinc hydroxide, zinc iodide, zinc nitrate, zinc oxide, zinc sulfate, or mixtures thereof. Many other transition metal enhancers are within the scope of the present invention. This section merely serves to illustrate some of the possible transition metal enhancers that are suitable to the methods according to the present invention.

In a preferred embodiment, the transition metal enhancers of the present invention are free metals, complexes, adducts, clusters, and/or salts of zinc, copper, nickel, cobalt, aluminum or gallium.

Transition metal enhancers that are especially preferred include zinc and copper containing compounds. More preferably, the transition metal enhancer is a zinc, nickel, cobalt, copper, aluminum or gallium halide. In yet an even more preferred embodiment, the transition metal enhancer is $ZnCl_2$, $NiCl_2$, $CoCl_2$, $CuCl_2$, $AlCl_2$, or $GaCl_2$. Even more preferably the transition metal enhancer is zinc acetate, zinc chloride, or zinc sulfate.

In other embodiments, the transition metal enhancer is a zinc ammonium complex together with its counter ion, zinc antimonide, zinc arsenate, zinc arsenide, zinc arsenite, zinc benzoate, zinc borate ($Zn_2B_6O_{11}$), zinc perborate, zinc bromide, zinc butyrate, zinc carbonate, zinc chromate, zinc chrome, zinc chromite, zinc citrate, zinc decanoate, zinc dichromate, zinc dimer, zinc ethylenebis(dithiocarbamate), zinc fluoride, zinc formate, zinc gluconate, zinc glycerate, zinc glycolate, zinc hydroxide, zinc iodide, zinc lactate, zinc methoxyethoxide, zinc naphthenate, zinc nitrate, zinc nitrate hexahydrate, zinc nitrate trihydrate, zinc octanoate, zinc oleate, zinc oxide, zinc pentanoate, zinc perchlorate hexahydrate, zinc peroxide, zinc phenolsulfonate, zinc propionate, zinc propylenebis(dithiocarbamate), zinc stannate, zinc stearate, zinc sulfate, zinc titanate, zinc tetrafluoroborate, zinc trifluoromethanesulfonate, and enhancers thereof.

The delivery of a nucleic acid and a transition metal enhancer is carried out using techniques known in the art of biotechnology as described below.

5.2 Buffers Useful For Nucleic Acid Delivery

The optimal pH range for a nucleic acid/transition metal enhancer mixture may vary depending upon the composition of the nucleic acid, the type of transition metal enhancer, and the particular cell type receiving the mixture.

In one embodiment, the nucleic acid/transition metal enhancer solution is not buffered. In other embodiments, however, the solution may be buffered. One or more buffers may be used, for example, to provide stable conditions for storage of the nucleic acid/transition metal enhancer mixture for an extended duration. Any buffer or pH not subjecting the nucleic acid to any condition of degradation may be used in the methods of the present invention. If nonnaturally occurring nucleic acids are used, the desirable buffer may be one that is substantially different than those used in conventional gene therapy. Representative buffers that could be used to buffer the nucleic acid/transition metal enhancer mixture of the present invention include, but are not limited to, N-[carbamoylmethyl]-2-aminoethanesulfonic acid (ACES), N-2[2-acetamido]-2-iminodiacetic acid (ADA), 2-amino-2-methyl-2,3-propanediol, 2-amino-2-methyl-1-propanol, 3-amino-1-propanesulfonic acid, 2-amino-2-methyl-1propanol, 3-[(1,1-dimethyl-2-hydroxyethyl)amino]-2-hydroxypropanesulfonic acid (AMSO), N,N-bis[2-hydroxyethyl]-2-aminoethanesulfonic acid (BES), N,N-bis[2-hydroxyethyl]glycine (BICINE), bis[2-hydroxyethyl]iminotris-[hydroxymethyl]methane (BIS-TRIS); 1,3-bis[tris(hydroxymethyl)-methylamino]propane (BIS-TRIS PROPANE), 4-[cyclohexylamino]-1-butanesulfonic acid (CABS), 3-[cyclohexylamino]-1-propanesulfonic acid (CAPS), 3-[cyclohexylamino]-2-hydroxy-1-propanesulfonic acid (CAPSO), 2-[N-cyclohexylamino]ethanesulfonic acid (CHES), 3-[N,N-bis(2-hydroxyethyl)amino]-2-hydroxypropanesulfonic acid (DIPSO), N-[2-hydroxy-ethyl]-piperazine-N'-[3-propanesulfonic acid] (HEPPS), N-[2-hydroxyethyl]piperazine-N'-[4-butanesulfonic acid] (HEPBS), N-[2-hydroxyethyl]piperazine-N'-[2-ethanesulfonic acid] (HEPES), N-[2-hydroxyethyl]piperazine-N'-[2-hydroxypropanesulfonic acid] (HEPPSO), imidazole, 2-[N-morpholino]ethanesulfonic acid (MES), 4-[N-morpholino]butanesulfonic acid (MOBS), 3-[N-morpholino]propanesulfonic acid (MOPS), 3-[N-morpholino]-2-hydroxypropanesulfonic acid (MOPSO), piperazine-N,N'-bis[2-ethanesulfonic acid] (PIPES), piperazine-N,N'-bis[2-hydroxypropanesulfonic acid] (POPSO), N-tris[hydroxymethyl]methyl-4-aminobutanesulfonic acid (TABS), N-tris[hydroxymethyl]methyl-3-aminopropanesulfonic acid (TAPS), 3-[N-tris(hydroxymethyl)methylamino]-2-hydroxy-propanesulfonic acid (TAPSO), triethanolamine (TEA), N-tris[hydroxymethyl]methyl-2-aminoethanesulfonic acid (TES), N-tris[hydroxymethyl]methylglycine (TRICINE), triethanolamine, tris[hydroxymethyl]aminomethane (TRIZMA) phosphate, acetate, citrate, borate, and bicarbonate.

Furthermore, the buffers may be in the form of the free acid, base or salt. For example, if the buffer used occurs as an acid, the buffer may be, for example, in the form of the acid, sodium salt, disodium salt, hemisodium salt, sodium salt hydrate, potassium salt, dipotassium salt, sesquisodium salt, or any other salt. If the buffer occurs as a base, the buffer may be, for example, in the form of the free base or as the hydrochloride. Other buffers may be used to buffer the nucleic acid/transition metal enhancer solution and the buffers provided herein merely serve to illustrate representative embodiments of the present invention.

In a preferred embodiment of the presently disclosed method, the nucleic acid/transition metal enhancer mixture is not buffered and the pH is not regulated. In a more preferred embodiment, the pH of the buffer is between about 4.0 and about 9.0. Even more preferably, the pH is between about 5.5 and 8.5.

5.3 Ratio of Transition Metal Enhancer to Nucleic Acid in the Nucleic Acid/Transition Metal Enhancer

5.3.1 Ratio of Nucleic Acid to Transition Metal Enhancer and Preferred Concentrations of Transition Metal Enhancer The ratio of transition metal enhancer to nucleic acid in the nucleic acid/transition metal enhancer mixtures of the present invention can vary over a tremendous range because of the large range in nucleic acid size that may be used in the present invention. Thus, depending on the size of the nucleic acid introduced, the ratio of transition metal enhancer to nucleic acid may be about one mole of transition metal enhancer per ten thousand moles of nucleic acid in the mixture to about one mole of transition metal enhancer per 0.0001 moles of nucleic acid in the formulation. Alternatively, the amount of transition metal enhancer relative to nucleic acid in the formulation may be calculated relative to the number of base pairs present in the formulation. In such instances, the amount of transition metal enhancer in the formulation may range from about one mole of transition metal enhancer for every ten thousand moles of base pairs in the formulation to about one mole of transition metal enhancer for every 0.0001 moles of nucleic acid in the formulation.

In a preferred method of computation, the amount of transition metal enhancer and the amount of nucleic acid present in the nucleic acid/transition metal enhancer mixture are considered independent. The concentration of the transition metal enhancer in the nucleic acid/transition metal enhancer mixture may range from about 0.01 mM to 250 mM if the mixture is in liquid form. More preferably, the concentration of the transition metal enhancer in the mixture is about 0.1 mM to about 6.0 mM. If the mixture is a lyophilized powder, the concentration of transition metal enhancer in the reconstituted mixture is about 0.01 mM to 250 mM. More preferably, the concentration of the transition metal enhancer in the reconstituted mixture is 0.1 mM to about 6.0 mM.

Some of the transition metals of the present invention, such as zinc, are essential trace elements that are present in most life forms. Therefore, it is expected that some of the transition metal enhancers of the present invention may be found in most bodily fluids and other in vivo environments. However, the concentrations of transition metal enhancer used in the present invention are considerably higher than the concentrations of transition metal enhancers that are found in a natural in vivo environment. For example, although dependent on a person's diet, the amount of zinc in human blood is about 880 $\mu$g/100 mL or about 0.135 mM. See, e.g., Altman et al., Blood and Other Body Fluids, Federation of American Societies for Experimental Biology. Such a concentration is considerably less than the concentrations of transition metal enhancer required in the nucleic acid/transition metal enhancer mixtures of the present invention.

5.3.2 Amount of Nucleic Acid Administered

The amount of nucleic acid applied according to the methods of the present invention will vary greatly according to a number of factors including, but not limited to, the susceptibility of the target cells to nucleic acid uptake, the levels of protein expression desired, if any, and the clinical status requiring the gene therapy. For example, the amount of nucleic acid injected into a salivary gland of a human is generally from about 1 $\mu$g to 200 mg, preferably from about 100 $\mu$g to 100 mg, more preferably from about 500 $\mu$g to 50 mg, most preferably about 20 mg. The amount of nucleic acid injected into the pancreas of a human may be, for example, from about 1 $\mu$g to 750 mg, preferably from about 500 $\mu$g to 500 mg, more preferably from about 10 mg to 200 mg, most preferably about 40 mg. The amounts of nucleic acid suitable for human gene therapy may be extrapolated from the amounts of nucleic acid effective for gene therapy in an animal model. For example, the amount of nucleic acid for gene therapy in a human is known to be about one to two hundred times the amount of nucleic acid effective in gene therapy in a rat. Furthermore, the amount of nucleic acid necessary to accomplish cell transfection will decrease with a corresponding increase in the efficiency of the transfection method used. In one preferred embodiment, the total concentration of the nucleic acid in the final mixture is from about 0.1 $\mu$g/ml to about 15 mg/ml.

5.3.3 Amount of Cationic Lipid Administered

In some embodiments of the present invention, the nucleic acid is mixed with cationic lipids and transition metal to form a cationic lipid/DNA/transition metal mixture. The cationic lipid/DNA/transition metal mixture is then used to transfect target cells of interest. In particular, it has been found that the use of cationic lipids in combination with a transition metal is particularly useful for the in vitro transfection of nucleic acids.

In embodiments in which a nucleic acid is delivered to target cells in the form of a cationic lipid/DNA/transition metal mixture, preferred nucleic acid concentrations range from 0.1 to 25 $\mu$g/$\mu$L. More preferably, the nucleic acid concentration is from 0.5 to 10 $\mu$g/$\mu$L. Furthermore, the transition metal concentration is preferably from about 0.01 to about 10 mM. However, the precise range of useful transition metal concentration range is largely determined by the unique characteristics specific transition metal used, such as solubility.

The present invention encompasses liposome solutions containing (i) a single form of cationic lipid, (ii) lipid mixtures that include a cationic lipid component and a neutral lipid component, or (iii) mixtures of different cationic lipids. An example of a lipid mixture that includes a cationic lipid component and a neutral lipid component is a mixture of dioleoylphosphatidyl ethanolamine and cholesterol. As used herein, the term cationic lipid is broadly construed and includes, but is not limited to, any lipid that contains functionality, such as primary amine, secondary amine, tertiary amine, or quaternary ammonium group, having a net positive charge at a useful physiological pH. Examples of cationic lipids include 1:1 N,N-[Bis(2-hydroxyethyl)]-N-methyl-N-[2,3-bis(tetradecanoyloxy) propyl]ammonium chloride and N,N,N',N'-tetramethyl-N, N'-bis(2-hydroxyethyl)-2,3-bis(9(z)-octadecenoyloxy)-1,4-butanediaminium iodide. Additional cationic lipids can be found in references such as *The Lipid Handbook,* Gunstone, Harwood, and Padley (Eds.), Second Edition, July 1994, CRC Press.

In some embodiments of the present invention, the amount of liposome present in cationic lipid/DNA/transition metal mixture is expressed in terms of the cationic lipid::DNA phosphate charge ratio. Illustrative complexes include those having a charge ratio of 0.5, 0.75, 1.0, and 2.0. Preferably, the cationic lipid:DNA phosphate charge ratio ranges from 0.01 to 12. More preferably, the lipid:DNA phosphate charge ratio ranges from 0.1 to 6. Even more preferably, the lipid:DNA phosphate charge ratio ranges from 0.5 to 4.

An important advantage of the present invention over prior art systems is that liposomes having low lipid:DNA phosphate charge ratios (i.e. less than 1) are still efficacious in delivering nucleic acids to cells.

5.4 Nucleic Acids That Can Be Delivered

Nucleic acids that may be used to form the nucleic acid/transition metal enhancers described in the present invention include DNA, DNA vectors, RNA, and synthetic oligonucleotides. All of these nucleic acids may either occur naturally or may be constructed or modified by the techniques known in the art of molecular biology and chemistry. The nucleic acids may exist as a circular or linear form, or alternatively, may be branched. The nucleic acid may be single stranded, double stranded, or may form other, more complex structures. The nucleic acid may carry a positive, neutral, or negative charge, although it will most preferably have a negative charge. In a preferred embodiment, there is no limit on the size range of the nucleic acids. In an even more preferred embodiment the nucleic acid will be from about 10 to about 20,000 nucleotides in length. In one preferred embodiment the nucleic acid will be from about 100 to about 10,000 nucleotides. In an even more preferred embodiment, the nucleic acid will comprise from about 500 to about 5,000 nucleotides.

5.4.1 Use of DNA Vectors as the Source of Nucleic Acid

The DNA vectors that can be used to form the nucleic acid/transition metal enhancer mixtures according to the present invention will typically be constructed from heterologous DNA sources using standard recombinant DNA techniques well known in the art. Various known vectors, such as DNA viral vectors, bacterial vectors, and vectors capable of replication in both eukaryotic and prokaryotic hosts, can be used in accordance with the present invention. Depending on the desired result, the vectors may contain sequences that mediate the stable integration of the vector DNA into a specific site in a particular chromosome. Such integration may provide the possibility for long-term, stable expression of genes contained within the vectors and/or enable a change in the genome that is beneficial. Alternatively, the vectors may be designed so that they do not insert into the cellular genome. Vectors that do not insert into the genome may or may not contain sequences to allow them to replicate within the cell. Thus, by varying the components included within the sequence of the DNA vectors, the stability and copy number of the vectors in the cells can be controlled as desired.

The vectors useful for the present invention will typically contain one or more genes or gene fragments of interest to allow the expression of one or more gene products following transfer of the vector into a target cell. In addition to these genes, vectors may also contain one or more marker genes to allow for selection, under specific growth conditions, of cells containing the vector DNA or to allow cells carrying vector sequences to be identified. Expression of an introduced gene or gene fragment can be controlled in a variety of ways, depending on the desired result and the construction of the vector. The gene may be expressed constitutively at various levels in the cells, or it may be expressed only under specific physiologic conditions or in specific cell types. Expression depends on the presence of a promoter region upstream from the gene, and may also be controlled by enhancer regions and other regulatory elements within the vector or within adjacent regions of the genomic DNA. The construction of DNA vectors for gene therapy and the components necessary for replication of the vectors, for insertion of the vectors into the cell genome, and for expression of genes carried by the vectors is well known in the art. See Curiel et al., Am. J. Respir. Cell Mol. Biol. 14:1, 1996; German et al., U.S. Pat. No. 5,837,693.

The primary expression product from a gene carried by a DNA vector is RNA. If the targeted cells are deficient in a particular transfer RNA or ribosomal RNA, the vector may complement this defect directly by providing a gene encoding the desired transfer or ribosomal RNA. Most typically, however, the RNA expressed from the gene carried by the vector DNA will function as a messenger RNA and encode a protein or protein fragment. Depending on the targeting sequences contained within the primary structure of the protein, the expressed protein will either be secreted from the cell, will be transported to one of the intracellular organelles, or will remain in the cytosol. Amino acid sequences within the expressed protein may also direct other modifications to the protein during or after translation of the protein. Proteins expressed from vector DNA may provide a therapeutic effect to the targeted cell or to other cells in the organism.

Depending on the sequence and stability of an RNA produced from a gene carried by the DNA vector, the RNA may also have antisense activity within the cell. Antisense oligonucleotides are typically designed to bind specifically to mRNA molecules within the cell to increase or decrease the stability or translation efficiency of the bound mRNA. It will be appreciated by those of skill in the art, however, that other forms of nucleic acid, including other RNA molecules and genomic DNA, may also be targeted by antisense methods. The target sequence to which an antisense RNA is complementary may be derived from a virus or a pathogenic microorganism, and expression of the antisense RNA encoded by a DNA vector and delivered into a target cell by methods of the invention may provide protection and/or a cure from infection caused by the virus or pathogenic microorganism. Alternatively, the target sequence to which the antisense RNA is complementary may be encoded by the target cell itself, and expression of the antisense RNA may protect an organism from disease states caused by abnormal expression of a targeted gene in the targeted cell. Target genes may include the various oncogenes and proto-oncogenes, as well as genes coding for the amyloid-like protein associated with Alzheimer's disease, the prion protein, and others. See Padmapriya et al., U.S. Pat. No. 5,929,226.

The RNA produced from the gene carried by the DNA vector may also function as a ribozyme. Ribozymes are RNA molecules that catalyze the hydrolysis of phosphodiester bonds in other RNA molecules. They can thereby inhibit and/or reduce the activity of a target RNA to which they bind. Ribozymes offer two significant advantages over antisense RNA molecules in gene therapy. First, because the activity of a ribozyme is catalytic, and a single ribozyme molecule can, therefore, cleave many target RNAs, ribozymes may be more efficient than antisense RNAs and may, therefore, be effective at lower concentrations. Second, because single mismatches can disrupt the catalytic activity of a ribozyme but would not necessary disrupt the binding of an antisense RNA to non-target RNA, the specificity of action of a ribozyme is greater than that of an antisense RNA. See Chowrira et al., U.S. Pat. No. 5,837,855.

5.4.2 Use of RNA as the Source of Nucleic Acid

Although it is possible to express an RNA of interest as derived from genes carried by DNA vectors, it may be desirable for purposes of the invention to use RNA itself to form the nucleic acid/transition metal enhancer mixtures. Large quantities of RNA can typically be generated by transcription from linear DNA templates using various RNA polymerases in a cell-free system. The DNA templates are constructed to encode the desired RNA sequences using techniques known in the art of molecular biology. The gene to be expressed is generally flanked by an RNA polymerase-specific promoter on its 5'end and a template encoding a polyA tail and transcription termination sequences on its 3'end. The gene is transcribed by RNA polymerase in the presence of a 5'cap and the four nucleoside triphosphates. It may be desirable to purify the RNA following its transcription to remove the polymerase and unincorporated small molecules. In addition, various chemical and enzymatic methods can be used to modify the RNA molecules included in the nucleic acid/transition metal enhancer solutions in order to protect them from nuclease digestion and to increase their stabilities within cells. Possible methods include end modification and circularization. See Felgner et al, U.S. Pat. No. 5,703,055.

RNA generated in any manner can be used to produce nucleic acid/transition metal enhancer mixtures and be delivered to target cells as provided by the methods of the invention. Transfer and ribosomal RNAs can be delivered into cells lacking sufficient quantities of these molecules. Likewise, messenger RNAs can be delivered into cells to allow expression of their encoded proteins. In addition, antisense RNA molecules and ribozymes produced by RNA polymerase can be delivered to target cells to provide any desired therapeutic effect.

RNA in the form of retroviral vectors or modified retroviral vectors can also be used to form the nucleic acid/transition metal enhancer mixtures of the invention. Retroviruses carry their genetic information in the form of RNA and can be used to express genes or gene fragments of interest in eukaryotic cells. Upon entering a cell, the retroviral RNA is reverse transcribed into DNA, and the DNA is subsequently inserted into the genomic DNA of the infected cell. Genes or gene fragments carried by a retrovirus and placed under the control of an appropriate promoter can, therefore, be expressed in cells as described above for DNA vectors.

5.4.3 Use of Synthetic Oligonucleotides and Analogues as a Source of Nucleic Acid The methods according to the present invention may also be performed using synthetic oligonucleotides and/or analogues to generate nucleic acid/transition metal enhancer mixtures. In particular, oligonucleotides synthesized by standard solid-phase chemical methods may be used. These molecules may additionally contain non-natural nucleic acid base analogues, sugar analogues, or linkages, or they may be modified by chemical means prior to formation of the mixtures. These alterations may result in an improvement in one or more desired properties for the oligonucleotides, such as an improved delivery of the oligonucleotides into target cells or an increased stability of the oligonucleotides within the cells. See Padmapriya et al., U.S. Pat. No. 5,929,226.

The heterocyclic bases of the oligonucleotide may include the naturally occurring bases (adenine, cytosine, guanine, thymine, and uracil) or may include synthetic modifications or analogues of these bases. The sugar component of the oligonucleotide may include the naturally occurring sugars (ribose and 2'-deoxyribose) or may include synthetic modifications or analogues of these sugars. In addition, the anomeric configuration of the sugar and even the position of coupling of the base to the sugar can be natural or non-natural in the oligonucleotides used to make the nucleic acid/transition metal enhancer mixtures of the invention. Finally, the linkage between nucleosides, modified nucleosides, or nucleoside analogues within the oligonucleotide may include the naturally occurring linkage (5' to 3' phosphodiester) or may include synthetic modifications or analogues of this linkage. Those skilled in the art will recognize that a large number of nucleosides, modified nucleosides, and nucleoside analogues are known in the prior art, and that any of these can be used alone or in combination to generate oligonucleotides for use in the nucleic acid/transition metal enhancer mixtures contemplated in the invention.

The design and synthesis of an oligonucleotide will likewise vary depending on the desired effects of the oligonucleotide within the cell. As described above for antisense RNA, antisense oligonucleotides can be designed to bind specifically to a target mRNA, and the binding may increase or decrease the stability or translation efficiency of the bound mRNA. Depending on the target, the method can potentially be used to control infection by a virus or pathogenic microorganism or can be used to regulate the growth of cells having desirable or undesirable properties. Alternatively, an oligonucleotide may be designed to recognize and bind to double-stranded DNA, and the triple helix formed as a consequence of this binding may alter expression of a gene targeted by the method. Finally, oligonucleotides delivered into a cell by the methods of the invention may have new functions, such as a novel catalytic activity or binding ability, and should not be limited to those functions known in the prior art.

5.5 Administration of the Nucleic Acid/Transition Metal Enhancer Mixture

In some embodiments of the present invention, such as embodiments directed to in vivo gene therapy methods, the nucleic acid/transition metal enhancer mixture may be directly administered to the cells within the organism of interest. In this instance, the dosage to be administered varies with the condition and size of the subject being treated as well as the frequency of treatment and the route of administration. Desirable regimens for chronic therapy protocols, including suitable dosage and frequency of administration, may be guided by the subjects initial response to the enhancer in view of sound clinical judgment. In some embodiments, the parenteral route of injection into the interstitial space either directly or via the bloodstream is used, although other parenteral routes, such as inhalation of an aerosol formulation, may be required in the administration to specific cells, as for example to the mucous membranes of the nose, throat, bronchial tissues or lungs.

In a preferred embodiment, a formulation comprising the nucleic acid and transition metal enhancer in a aqueous carrier is injected in vivo into the tissue in amounts of from about 10 µl per site to about 100 ml per site.

5.6 Representative Nucleic Acid Delivery Methods to Various Tissues

5.6.1 Nucleic Acid Delivery to Secretory Glands

The methods of the present invention may be used to deliver nucleic acids to various secretory glands using routes of administration such as, for example, those described by German et al., U.S. Pat. No. 5,885,971. As used herein, a secretory gland is defined as aggregation of cells specialized to secrete or release materials not related to their ordinary metabolic needs. Secretory glands may include salivary glands, pancreas, mammary glands, thyroid gland, thymus gland, pituitary gland, liver, and other glands well known to one skilled in the art.

In one embodiment, the methods of the present invention are used to deliver nucleic acids to salivary glands. Salivary glands are defined herein as any gland of the oral cavity that secretes saliva, including the glandulae salivariae majores of the oral cavity (collectively, the parotid, sublingual, and submandibular glands) and the glandulac salivariae minores of the tongue, lips, cheeks, and palate (labial, buccal, molar, palatine, lingual, and anterior lingual glands).

The routes of administration, described by German et al., for the presently claimed nucleic acid/transition metal enhancer mixture may include administration according to known in vivo or ex vivo methods. When in vivo methods are used, the nucleic acid/transition metal enhancer mixture may be injected directly into a secretory gland or into a secretory gland duct. The subsequent exposure of the secretory gland to the nucleic acid/transition metal enhancer mixture results in the uptake of the nucleic acid by the target cells present within the aggregation comprising the secretory gland.

Alternatively, if ex vivo methods are used to introduce nucleic acid to any of the described secretory glands, a biopsy of secretory gland tissue may be obtained from the organism of interest. In a preferred embodiment, the organism is a mammal. Preferably, the biopsy is used to establish a primary cell culture. The biopsy tissue or the primary cell culture then receives the nucleic acid/transition metal enhancer mixture, resulting in the uptake of the nucleic acid in to the internal cellular environment of the secretory gland cells. Cells that have been exposed to the nucleic acid/transition enhancer metal mixture are then reintroduced into the secretory gland within the organism.

When the nucleic acid contains certain types of retroviral sequences known to those skilled in the art, a portion of the nucleic acid may also be incorporated into the genome of the secretory gland cells. The incorporation of the exogenous nucleic acid into the genome of the secretory gland cell typically results in the stable transcription of a portion of nucleic acid that is operably linked to a promoter. In a preferred embodiment, however, the nucleic acid in the nucleic acid/transition metal enhancer mixture does not contain any retroviral sequences and is only transiently transcribed.

If the nucleic acid is transcribed by the cell, and codes for a polypeptide, the polypeptide may be then expressed by the cellular machinery after gene delivery. The polypeptide may be a functional protein and may be secreted by the secretory cells into the bloodstream, gastrointestinal system or interstitial spaces or any other internal or external compartment of the organism. Therefore, the methods of the present invention could be used to supplement various proteins of interest in the bloodstream with the host organism by the addition of the newly transcribed peptide product. Such an application offers utility in treatment of a wide variety of diseases such as, for example, those described by German et al., U.S. Pat. No. 5,837,693. Accordingly, representative examples of proteins that may be encoded by the nucleic acid in the nucleic acid/transition metal enhancer mixture include, but are not limited to, insulin, human growth hormone, erythropoietin, clotting factor VII, bovine growth hormone, platelet derived growth factor, clotting factor VIII, thrombopoietin, interleukin-1, interluekin-2, interleukin-1 RA, superoxide dismutase, catalase, fibroblast growth factor, neurite growth factor, granulocyte colony stimulating factor, L-asparaginase, uricase, chymotrypsin, carboxypeptidase, sucrase, calcitonin, Ob gene product, glucagon, interferon, transforming growth factor, ciliary neurite transforming factor, insulin-like growth factor-1, granulocyte macrophage colony stimulating factor, brain-derived neurite factor, insulintropin, tissue plasminogen activator, urokinase, streptokinase, adenosine deamidase, calcitonin, arginase, phenylalanine ammonia lyase, γ-interferon, pepsin, trypsin, elastase, lactase, intrinsic factor, cholecystokinin, and insulinotrophic hormone.

5.6.2 Nucleic Acid Delivery to the Brain

The methods according to the present invention may be used to deliver a nucleic acid to various desired regions of brain tissue using routes of administration as described by U.S. Pat. No. 5,580,859 to Felgner et al. and U.S. Pat. No. 5,916,803 to Sedlacek et al. As used herein, brain tissue is generally defined as an aggregation of cells, including, but not limited to neurons, Schwann cells, glial cells and astrocytes. Such cells are known to contain properties which are specialized to perform various functions associated with the central or peripheral nervous systems. Preparations to be used according to the methods of presently claimed invention may also be introduced into various nerve cells using known approaches described previously.

In one embodiment, brain tissue may be isolated from adult mice following injection of a gene construct comprising a sequence encoding, for example, a polypeptide as described above. In one embodiment, a promoter is operably associated with a sequence encoding a molecule, such as a polynucleotide. More specifically, other molecules which may be practiced according to the present invention may be polynucleotides including genomic DNA, cDNA, and mRNA that encode therapeutically useful proteins known in the art, ribosomal RNA, antisense RNA or DNA polynucleotides, that are useful to inactivate transcription products of genes, or even retroviral nucleic acid. The injections may be administered through various administration routes as described herein to a desired region, for example, into each of the bilateral parietal, frontal, temporal or visual cortex regions. Following injection of the genetic material, the tissue may be assayed in accordance with the methods disclosed herein. Successful introduction of the genetic material upon analysis of gene expression may provide necessary information to direct therapeutic strategies such as, for example, to induce, enhance and/or inhibit the formation, growth, proliferation, differentiation, maintenance of neurons and/or related neural cells and tissues such as brain cells, Schwann cells, glial cells and astrocytes.

As previously described, the nucleic acid may contain any of the desired retroviral sequences or various exogenous nucleic acid sequences that are able to be incorporated into the genome of the nerve cell, thereby resulting in the stable transcription of a portion of nucleic acid. In a preferred embodiment, however, the nucleic acid in the nucleic acid/transition metal enhancer mixture does not contain any retroviral sequences and is only transiently transcribed. Alternatively, the nucleic acid codes for a polypeptide that may be expressed by the cellular machinery. The polypeptide may be a functional protein and may be secreted by the nerve cells into the interstitial spaces within the brain. Therefore, the methods of the present invention may be used to supplement various proteins present within the host organism by the addition of the newly transcribed peptide product in a manner as described above.

Another embodiment of the present invention is a therapeutic method and composition for treating disorders of neurons and/or related neural cells and tissues associated with Schwann cells, glial cells and astrocytes, and other conditions related to neuronal and neural tissue disorders or diseases. The invention is further directed to therapeutic methods for repair and restoration of nerve tissue.

It is further contemplated that the methods of the present invention may increase neuronal, glial cell and astrocyte survival and therefore have great utility in known transplantation protocols for the treatment of conditions known to cause a decrease in neuronal survival.

5.6.3 Nucleic Acid Delivery to Muscle

The methods of the present invention may be used to deliver a nucleic acid to various desired regions of muscle tissue using routes of administration as described by U.S. Pat. Nos. 5,580,859 and 5,916,803. As used herein, muscle tissue is generally defined as an aggregation of cells, which comprise the bulk of the body's musculature including, but not limited to cardiomyocytes, skeletal and smooth muscle cells. Such cells are known to have properties which are specialized to perform various functions commonly associated with movement as well as other known functions of the muscular system. Preparations to be used according to the methods of the presently claimed invention can also be introduced into various muscle cells using known approaches described above.

In one embodiment, muscle tissue may be isolated from adult mice following injection of a gene construct comprising a sequence encoding, for example, a polypeptide. In one embodiment, a promoter is operably associated with a sequence encoding the polypeptide. More specifically, other molecules which may be practiced according to the present invention may be similar to those described previously.

Administration of the nucleic acid/transition metal enhancer mixture according to the present invention may be to a desired region, such as a particular muscle group within the organism, or a particular location within such a muscle group. Following injection of the genetic material, the muscle tissue may be assayed in accordance with the methods described previously. Successful introduction of the genetic material as demonstrated by measurable gene expression may provide information useful for developing therapeutic strategies such as, for example, to induce, enhance and/or inhibit the formation, growth, proliferation, differentiation, maintenance of the various cells of the skeletalmuscular system, including cardiomyocytes, skeletal and smooth muscle cells.

As previously described, the nucleic acid may contain any of the desired retroviral sequences or various exogenous nucleic acid sequences that are able to be incorporated into the genome of the muscle cell, thereby resulting in the stable transcription of a portion of the nucleic acid. In a preferred embodiment, however, the nucleic acid in the nucleic acid/transition metal enhancer mixture does not contain any retroviral sequences and is only transiently transcribed. Alternatively, the nucleic acid codes for a polypeptide that may be expressed by the cellular machinery. The polypeptide may be a functional protein and may be secreted by the muscle cells into the interstitial spaces of the brain. Therefore, the methods of the present invention may be used to supplement various proteins present within the host organism by the addition of the newly transcribed peptide product in a manner as described above.

Another embodiment of the present invention is a therapeutic method for treating disorders of myocytes and/or related muscle cells and tissues such as cardiomyocytes, skeletal and smooth muscle cells, and any other condition related to a muscular tissue disorder or disease. The invention is further directed to therapeutic methods for repair and restoration of muscular tissue.

It is further contemplated that the methods of the present invention may increase muscle cell survival and therefore be useful in known transplantation procedures and for the treatment of conditions known to cause any degeneration in related tissues.

5.6.4 Nucleic Acid Delivery to the Pancreas

The methods of the present invention may be used to deliver a nucleic acid to various desired regions of pancreatic tissue using routes of administration as described by U.S. Pat. Nos. 5,580,859 and 5,916,803. As used herein, pancreatic tissue is defined as comprising an endocrine portion (the pars endocrina) and an exocrine portion (the pars exocrina). The pars endocrina, contains the islets of Langerhans, and the pars exocrina contains acinar cells. The pancreas is generally defined as an aggregation of cells, which comprises the entire pancreatic structure, including but not limited to ductal cells, acinar cells, beta cells, alpha cells, and other cells of the Islets of Langerhans. Such cells are known to have properties which are specialized to perform various functions commonly associated with digestive processes, hormonal regulation, and other known functions.

Compositions described according to the methods of the presently claimed invention can also be introduced into various pancreatic cells using known approaches described above. The routes of administration, described by German et al., for the presently claimed nucleic acid/transition metal enhancer mixture are used in accordance with known ex vivo or in vitro methods.

In one embodiment, pancreatic tissue may be isolated from adult mice following the successful injection of a gene construct composition in accordance with the present invention. The genetic construct may comprise a sequence encoding, for example, a polypeptide. In one embodiment, a promoter is operably associated with a sequence encoding the polypeptide. More specifically, other molecules which may be practiced according to the present invention may be similar to those described previously.

Administration of the nucleic acid/transition metal enhancer mixture according to the present invention may be to a desired region within the pancreatic structure, such as a specialized cell group within the pancreas. Following injection of the genetic material, the pancreatic tissue may be assayed in accordance with the known methods designed to quantitate protein levels or other methods for detecting increased gene expression. Successful introduction of the genetic material as demonstrated by measurable gene expression may provide information useful for developing therapeutic strategies such as, for example, to induce, enhance and/or inhibit the formation, growth, proliferation, differentiation, maintenance of the various cells of the pancreas, including acinar cells, beta cells, alpha cells, ductal cells, and other cells of the Islets of Langerhans.

If the nucleic acid is transcribed by the cell, and codes for a polypeptide, the polypeptide may be expressed by the cellular machinery after gene delivery. The polypeptide may be a functional protein and may be secreted by pancreatic cells into the bloodstream, gastrointestinal system or interstitial spaces or any other internal or external compartment of the organism. Therefore, the methods of the present invention could be used to supplement various proteins of interest in the bloodstream with the host organism by the addition of the newly transcribed peptide product. Such an application offers utility in treatment of a wide variety of diseases such as, for example, those described by German et al., U.S. Pat. No. 5,837,693. Accordingly, representative examples of proteins that my be encoded by the nucleic acid in the nucleic acid/transition metal enhancer mixture include, but are not limited to, insulin, human growth hormone, erythropoietin, clotting factor VII, bovine growth hormone, platelet derived growth factor, clotting factor VIII, thrombopoietin, interleukin-1, interleukin-2, interleukin-1 RA, superoxide dismutase, catalase, fibroblast growth factor, neurite growth factor, granulocyte colony stimulating factor, L-asparaginase, uricase, chymotrypsin, carboxypeptidase, sucrase, calcitonin, Ob Gene product, glucagon, interferon, transforming growth factor, ciliary neurite transforming factor, insulin-like growth factor-1, granulocyte macrophage colony stimulating factor, brain-derived neurite factor, insulintropin, tissue plasminogen activator, urokinase, streptokinase, adenosine deamidase, calcitonin, arginase, phenylalanine ammonia lyase, χ-interferon, pepsin, trypsin, elastase, lactase, intrinsic factor, cholecystorkinin, and insulinotrophic hormone.

Another embodiment of the present invention is a therapeutic method for treating disorders associated with pancreatic cell degeneration and any other condition related to a pancreatic tissue disorder or disease. The invention is further directed to therapeutic methods for repair and restoration of defective pancreatic tissue.

It is further contemplated that the methods of the present invention may increase pancreatic cell survival and therefore be useful in known transplantation procedures and for the treatment of conditions known to cause any degeneration in related tissues.

5.6.5 Nucleic Acid Delivery to Other Tissue Types

The present invention presents methods using a nucleic acid/transition metal enhancer mixture that facilitates intracellular delivery of therapeutically effective amounts of nucleic acid to target cells. The therapeutic enhancer and the method of use in gene delivery as presently claimed may be further suitable for use with other cell types including, but not limited to, cell groups associated with the breast, thyroid, bone, bladder, skin, liver, stomach, lung, kidney, gastrointestinal tract, and various reproductive organs such as the testes, uterus and ovaries. Successful introduction of the genetic material resulting in subsequent gene expression may provide useful information for developing therapeutic strategies such as, for example, to induce, enhance and/or inhibit the formation, growth, proliferation, differentiation, maintenance of the various cells of the tissues described above.

As previously described, the nucleic acid may contain any of the desired retroviral sequences or various exogenous nucleic acid sequences that are able to be incorporated into the genome of the muscle cell, thereby resulting in the stable transcription of a portion of the nucleic acid. In a preferred embodiment, however, the nucleic acid in the nucleic acid/transition metal enhancer mixture does not contain any retroviral sequences and is only transiently transcribed. Alternatively, the nucleic acid codes for a polypeptide that may be expressed by the cellular machinery. The polypeptide may be a functional protein and may be secreted by the muscle cells into the interstitial spaces within the brain. Therefore, the methods of the present invention may be used to supplement various proteins present within the host organism by the addition of the newly transcribed peptide product in a manner as described above.

5.7 Routes of Administration of the Nucleic Acid/Transition Metal Enhancer Solution The nucleic acid/transition metal enhancer mixture may be applied to target tissues and/or cells using any method capable of exposing, either directly or indirectly, nucleic acids into cells. One of skill in the art will appreciate that references describing routes of administration for "naked" (free) nucleic acid delivery are well suited for the methods of the present invention. It will be appreciated that any known representative administration methods may be adapted to practice the methods according to the present invention. In one embodiment, the nucleic acid/transition metal enhancer mixture may be administered intramuscularly using methods derived from, for example, Rivera et al., Proc. Natl. Acad. Sci. U.S.A. 96:8657, 1999, and/or McCluskie et al, Mol. Med. 5:287, 1999. Additionally, the nucleic acid/transition metal enhancer mixture may be administered intratracheally using methods adopted from those described by Bennett et al., J. Med. Chem. 40:4069, 1997, and/or Meyer et al, Gene. Ther. 2:450, 1995. In yet another embodiment, the nucleic acid/transition metal enhancer mixture may be administered intraperitoneally using methods adopted from those described by McCluskie et al., id., and/or Reimer et al., J. Pharmacol. Exp. Ther. 289:807, 1999. The nucleic acid/transition metal enhancer mixture may be also be administered intradermally using methods adopted from those described by McCluskie et al., id. and/or Watanabe et al., J. Immunol. 163:1943, 1999. In another embodiment, the nucleic acid/transition metal enhancer mixture may be administered intravenously using methods adopted from those described by McCluskie et al., id., and/or Wang et al., J. Clin. Invest. 95:1710, 1995. In still another embodiment, the nucleic acid/transition metal enhancer mixture may be administered intraperineally, subcutaneously, sublingually, via the vaginal wall, by intranasal instillation, intrarectally, ocularly, intraductally, or orally using adaptations of various methods described in McCluskie et al., id. In yet another embodiment, the nucleic acid/transition metal enhancer mixture may be administered by intranasal inhalation by adaptations of the methods described in McCluskie et al., id., or Kulkin et al., J. Virol., 71:3138, 1997. The nucleic acid/transition metal enhancer mixture may also be administered intravaginally using adaptations of methods described by McCluskie et al., id., or Wang et al., Vaccine 15:821, 1997. Additionally, the nucleic acid/transition metal enhancer mixture may be administered topically using adaptations of the route of administration described by Yu et al., J. Invest. Dermatol. 112:370, 1999.

5.8 Therapeutic Formulations

In one embodiment, the nucleic acid/transition metal enhancer mixture, according to the method of the present invention, may be prepared in unit dosage form provided in ampules, multidose containers, or other pharmaceutically accepted dosage forms. The nucleic acid/transition metal enhancer mixture may be present in such forms as suspensions, solutions, or emulsions in oily or preferably aqueous vehicles. Alternatively, the nucleic acid/transition metal enhancer mixture may be lyophilized to form a lyophilized product. The lyophilized product may be hydrated, at the time of delivery, with a suitable vehicle, such as sterile pyrogen-free water. Both liquid as well as lyophilized forms that may be reconstituted will comprise agents, preferably buffers, in amounts necessary to suitably adjust the pH of the injected solution. For any parental use, particularly if the formulation is to be administered intravenously, the total concentration of the solutes should be controlled to make the desirable preparation isotonic or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% nucleic acid.

The units dosage ampules or multidose containers, in which the nucleic acids are packaged prior to use, may comprise a hermetically sealed container enclosing an amount of nucleic acid or solution containing a nucleic acid suitable for a pharmaceutically effective dose thereof, or multiples of an effective dose. The polynucleotide is packaged as a sterile formulation, and the hermetically sealed container is designed to preserve the sterility of the formulation until use.

In a preferred embodiment, the container in which the nucleic acid/transition metal enhancer is packaged employs the usage of a Good Manufacturing Practice (GMP) compliant protocol and is appropriately labeled in accordance with applicable sections of the Federal Food, Drug, and Cosmetic Act (the "FDCA"; Title 21, United States Code).

6. EXPERIMENTS

6.1 Experimental Methods

The following experiments are intended to provide those of ordinary skill in the art with a disclosure and description of how to carry out the invention and is not intended to limit the scope of what the inventor regards as the invention.

6.1.1 Preparation and Purification of Reporter Genes

A DNA vector, pCMV.FOX.Luc-2 (FIG. 1), containing the firefly luciferase reporter gene (LUC) operably linked to human cytomegalovirus major immediate early enhancer/promoter was stably transfected into competent E. coli XL-1 blue cells (Stratagene, La Jolla, Calif.), cultured in Luria Bertani (LB) medium, and further isolated by alkaline lysis. The plasmid was subsequently passed through an anion exchange resin (Qiagen, Santa Clarita, Calif.) to yield an endotoxin-reduced, supercoiled plasmid. Once purified, the plasmid is suspended in a solution containing 10 mM Tris-HCl and 1 mM EDTA. The plasmid DNA, pBAT-iMG-2, containing the alpha-1 antitrypsin gene was prepared and purified using a similar procedure. The plasmid pCMV.FOX.hGH, containing the human growth hormone gene, was prepared and purified using a similar procedure.

6.1.2 Preparation of Nucleic Acid Solutions For In Vivo Transfection

Nucleic acid/transition metal enhancer mixtures were prepared by sequentially adding deionized water or a buffered solution, DNA, and a desired transition metal enhancer to a polystyrene tube with mixing. "Free" (i.e., "Naked") DNA controls were prepared by sequentially adding DNA to water or a buffered solution

6.1.3 Administration of Anesthesia

Intramuscular injection of mixtures comprising ketamine (30 mg/kg), xylazine (6.0 mg/kg) and aceproamzine (1.0 mg/kg) were administrated to all experimental animals.

6.1.4 Intraductal Delivery of Nucleic Acid/transition Metal Enhancer Into the Rat Salivary Gland Male Sprague-Dawley rats (260–280 g) were fasted the night prior to treatment. After administration of the anesthesia (see Section 6.1.3), both right and left salivary gland ducts (specifically, Wharton's duct) were cannulated with fine polyurethane tubing (i.d. 0.005") and cemented into the desired location. Atropine was then administered subcutaneously (0.5 mg/kg) and, after eight minutes, 50 $\mu$l of the nucleic acid/transition metal enhancer mixture was injected, infused, instilled or administered at the ductal orifice or directly into the duct at any point along its length. See Goldfine, Nature Biotechnology 15:1378, 1997.

In embodiments in which a liposome/transition metal/nucleic acid mixture was used, 200 $\mu$l of the liposome/transition metal/nucleic acid mixture was injected, infused, instilled or administered at the ductal orifice or directly into the duct at any point along its length. See Goldfine, Nature Biotechnology 15:1378, 1997. The liposome/transition metal/nucleic acid mixture was prepared by sequentially adding an appropriate amount of sterile water, liposome solution (3:1, N,N,N',N'-tetramethyl-N,N'-bis(2-hydroxyethyl)-2,3-bis(9(z)-octadecenoyloxy)-1,4-butanediaminium iodide (DOHBD):DOPE), transition metal enhancer, and the plasmid DNA pCMV.FOX.hGH to a polypropylene tube.

Regardless of whether a liposome/transition metal/nucleic acid mixture or a nucleic acid/transition metal enhancer mixture was delivered, the tubing and mixture was kept in place for ten additional minutes after application of the mixture prior to removal. At 48 hours post atropine administration, the rats were anesthetized by intraperitoneal injection of pentobarbital (50 mg/kg). The right and left submandibular glands were surgically removed, and the tissues were assayed for any observable reporter gene (luciferase of hGH) expression using the methods described below.

6.1.5 Luciferase Assay

The presently claimed invention describes a new method using a combination of a transition metal enhancer and a nucleic acid of interest for gene delivery. The present invention provides a method which may enhance gene expression by improving the efficiency of gene delivery. This change in gene expression can be quantitated using various assays, such as the luciferase assay. de Wet et al., Molec. Cell Biol. 7:725, 1987. In various experiments described herein, the right and left submandibular glands were removed from the male Sprague-Dawley rats at 48 hours post administration of the pCMV.FOX.Luc-2 containing solution. In additional experiments other organs, such as the rat lungs, were used.

In experiments in which submandibular glands were tested, the amount of luciferase present in the right and left submandibular gland of each male Sprague-Dawley rat was measured independently and treated as separate, individual experiments (e.g., trials) because the amount of luciferase expressed by one submandibular gland is independent of the amount of luciferase expressed in the other submandibular gland. Therefore, each submandibular gland was independently lysed in lysis buffer (1.0 ml buffer per 0.1 g tissue) to create a lysis homogenate. The lysis buffer contained 100 mM $K_2PO_4$ pH 7.0, 1 mM dithiothreitol, and 1% Triton X-100. A 100 μl aliquot of lysis homogenate from each submandibular gland was analyzed for luciferase activity (de Wet et al., Molec. Cell Biol. 7:725, 1987) using a Monolight 2010 luminometer (Analytical Luminescence Laboratories). Accordingly, luciferase light emissions from each aliquot of the lysis homogenate were measured over a ten second period.

Activity was expressed as relative light units, values collectively representing the assay conditions, luciferase concentration, luminometer photomultiplier tube sensitivity and background. Using well known techniques, the luciferase light units may be converted, for example, to picograms of luciferase protein. See, e.g., Felgner et al., U.S. Pat. No. 5,580,899 at Example 13. All experiments were performed in duplicate. In experiments using submandibular glands, data from each individual submandibular gland lysis homogenate is reported as a single trial. Results from multiple trials (n=4) are averaged and listed in Tables 1 through 8 below.

6.1.6. Intra-tracheal Delivery of DNA-Containing Products in the Mouse Lung

Male BALB/c mice (specific pathogen free, Charles River Laboratories; 20–21 g) were used in the transfection experiments. Anesthesia was provided for all invasive procedures; animals were terminated by intraperitoneal administration of pentobarbital according to standard protocols. Neck dissections were performed on anesthetized mice using a one centimeter incision through the skin of the anterior neck. Delivery of 150 μl of the nucleic acid/transition metal enhancer was performed using a half inch thirty gauge needle, inserted 1–3 tracheal ring interspaces inferior to the larynx. For comparison, a free nucleic acid solution (150 μl containing 512 μg of DNA) was prepared in sterile water and delivered in a similar manner. After injection, the point of incision was repaired using staples. The mice were terminated within 48 hours after treatment. A tracheal/lung block was dissected and then homogenized in chilled lysis buffer comprising 0.1M potassium phosphate buffer (pH 7.8), 1% Triton X-100, 1 mM dithiothreitol, and 2 mM EDTA, and assayed for luciferase activity.

6.1.7. Intraductal Instillation of DNA-Containing Products into the Rat Pancreas or Liver Male Sprague-Dawley rats (weighing 260–280 g) were fasted the night prior to treatment. Care was taken to ensure that this procedure was conducted under sterile conditions. After anesthesia (see above) and laparotomy, the distal end of the bile duct (at the level of the duodenum) was ligated, the proximal end of the pancreas (at the porta hepatis level) was temporary blocked by a ligature, a PE-10 tubing was inserted through an incision of the bile duct near the duodenum. 0.1 ml of the selected nucleic acid/transition metal enhancer mixture was injected in a retrograde manner into the duct. Successful injection was confirmed by visible swelling of the gland. For administration to the liver, the proximal portion of the bile duct (prior to its entry into pancreatic tissue) was injected. After DNA delivery, a by-pass operation was done by directly introducing the bile flow to duodenum through the exterior end of the PE-10 tubing. After carefully ensuring the ligatures were secure, 1 ml of ampicillin (15 mg/ml) was injected into the peritoneal cavity and the incision was closed in one layer, combining fascia and skin with 3-0 silk suture. The closed incision was washed with dilute ethanol and the animal was monitored under a heat lamp until it was fully awake and ambulatory. The mice were terminated 48 hours after treatment. The pancreas and liver were removed and individually homogenized in chilled lysis buffer, and assayed for luciferase activity.

6.1.8. Human Alpha-1 Antitrypsin Assay

Polystyrene 96-well plates (Costar #3590) were coated with primary coating antibody (rabbit polyclonal; Roche #605 002, diluted 1:1000, in 1 X carbonate buffer; use 100/well), and placed in humidified hybridization tray and incubate overnight in refrigerator (4° C.). The plate was then washed two times with PBS-T (phosphate buffered saline+ 0.5% Tween-20; 200/well), and blocked with PBS-T+1% BSA (200 μL/well) at room temperature for one hour. After three PBS-T washes, the test samples were added (100 μL/well) and incubated three hours at room temperature on a microplate shaker (500 rpm). After five PBS-T washes, the second antibody was added (goat polyclonal; ICN #55236, diluted 1:2000 in PBS-T+1% BSA; 100 μL/well), and incubated sixty minutes on a microplate shaker (500 rpm). The plate was then washed five times with PBS-T and the TMB substrate was added (Dako #S1600; 100 μL/well). The assay development required twenty minutes, and was monitored with a platereader set at 650 nm wavelength (Molecular Devices SpectraMax190, using SOFT max v 3.0 software). At this time, a 2N $H_2SO_4$ stop solution (100 μL/well) was added, and the final readings were taken at 450 nM.

6.1.9. Preparation of Liposome Solutions

In one embodiment, an appropriate mass of cationic lipid and the neutral lipid dioleoylphosphatidylethanolamine (DOPE) was added as solutions in chloroform to 1.9 mL sample vials to yield the desired molar ratio of cationic lipid:DOPE. The chloroform was removed via rotary evaporation at 37° C. The resulting thin lipid films were placed under vacuum overnight to insure that all traces of solvent have been removed. The lipid mixture was resuspended in 1 mL sterile water at 25° C. until the film is hydrated, and then vortex mixed to afford an emulsion. For the in vitro experiments, these emulsions were formulated as a cationic lipid concentration of 1 mM. For the in vivo experiments, the emulsions were formulated at a cationic lipid concentration of 3 mM.

6.1.10. Cell Culture

NIH 3T3 cells were obtained from ATCC (CRL 1658), cultured in Dulbecco's Modified Eagle's Medium with ten percent calf serum, and plated on standard 24 well tissue culture plates 24 hours prior to transfection. Cells were approximately eighty percent confluent at the time of transfection.

6.1.11. Transfection of Cultured Cells

NIH 3T3 cells were plated onto 24 well tissue culture plates as described in section 6.1.10. The growth media was removed via aspiration and the cells were washed once with 0.5 mL PBS/well. The liposome/transition metal/nucleic acid solutions were formed through sequential addition of appropriate amounts of DMEM (without serum), the liposome solution (1:1 N,N-[Bis(2-hydroxyethyl)]-N-methyl-N-[2,3-bis(tetradecanoyloxy)propyl] ammonium chloride (DMDHP):DOPE, zinc chloride, and the plasmid DNA pCMV.FOX.Luc.2. The amount of liposome solution used depended on the desired cationic lipid to DNA phosphate ratio. The addition of these substances was followed by thorough vortex mixing and incubation for 15 minutes at room temperature. A 200 microliter aliquot of the resultant transfection complex was added to each well (1 microgram DNA/well, n=4) and the cells were incubated for 4 hours, at 37° C. At this time, 500 microliters of DMEM+10% calf serum/well was added and the cells cultured for approximately 48 hours prior to lysis and analysis. The sample transfections were subsequently repeated a minimum of three times prior to lysis and analysis.

6.1.12 Luciferase Assay Using Cationic Lipid/Transition Metal Enhancer/Nucleic Acid Complexes The presently claimed invention describes a new method using a combination of cationic lipid, transition metal enhancer and a nucleic acid of interest for gene delivery. The present invention provides a method that may enhance gene expression by improving the efficiency of gene delivery. This change in gene expression can be quantitated using various assays, such as the luciferase assay. de Wet et al., Molec. Cell Biol. 7:725, 1987. In in vitro experiments described herein in which a cationic lipid/transition metal enhancer/nucleic acid complex was used, the cells were lysed, using a lysis buffer, 48 hours post administration of the pCMV.FOX.Luc-2 containing solution. The lysis buffer contained 100 mM $K_2PO_4$ pH 7.0, 1 mM dithiothreitol, and 1% Triton X-100. A 25 µl aliquot of the lysate was analyzed for luciferase activity (de Wet et al., Molec. Cell Biol. 7:725, 1987) using a Monolight 2010 luminometer (Analytical Luminescence Laboratories). Accordingly, luciferase light emissions from each aliquot of the lysis homogenate were measured over a ten second period. Activity was expressed as relative light units, values collectively representing the assay conditions, luciferase concentration, luminometer photomultiplier tube sensitivity and background. Using well known techniques, the luciferase light units may be converted, for example, to picograms of luciferase protein. See, e.g., Felgner et al., U.S. Pat. No. 5,580,899 at Example 13. Results from multiple trials (n=4) are averaged and listed in Table 10.

6.2 EXPERIMENTAL EXAMPLES

The following examples are provided to illustrate the methods of the presently claimed invention.

6.2.1 Example 1

Effect of DNA Dose on Zinc Chloride-Mediated Transfection

An experiment was performed to determine the optimal DNA dose for in vivo zinc chloride-mediated transfection. To perform this study, DNA/zinc mixtures, A-1 thru A-4, were prepared by mixing an appropriate amount of water, zinc chloride, and pCMV.FOX.Luc.2 plasmid DNA in a polystyrene tube. The relative amount of zinc chloride to DNA was maintained at 0.19 mg zinc chloride per 1 mg DNA. For comparison, DNA control solutions, B-1 thru B-4, were prepared in a similar manner except without zinc chloride. Both the DNA/zinc mixtures and the control solutions were screened for in vivo transfection activity at DNA doses of 32, 64, 96, 128 micrograms by using the rat salivary gland model as described above. Specifically, 50 µl of a particular DNA/zinc mixture or a DNA control solution was administered to both the right and the left submandibular gland of four male Sprague-Dawley rats. At 48 hours post administration, the glands were harvested and assayed for luciferase specific activity as described above. The average result obtained from each treatment condition examined in this study is presented in Table 1. The data illustrates that DNA/zinc mixtures show higher levels of transfection activity in the rat salivary gland relative to free DNA solutions. In addition, the data shows that the improved transfection activity is observed using several DNA doses and zinc concentrations.

TABLE 1

Effect of DNA Dose on Zinc Chloride-Mediated Transfection

| Solution | DNA Dose [µg] | $ZnCl_2$ | Buffer [mM] | Relative Light Units |
|---|---|---|---|---|
| A-1 | 32 | 0.9 | 1.6 | 57884 |
| A-2 | 64 | 1.8 | 3.2 | 145179 |
| A-3 | 96 | 2.7 | 4.8 | 192936 |
| A-4 | 128 | 3.6 | 6.4 | 756838 |
| B-1 | 32 | 0 | 1.6 | 24322 |
| B-2 | 64 | 0 | 3.2 | 31885 |
| B-3 | 96 | 0 | 4.8 | 59774 |
| B-4 | 128 | 0 | 6.4 | 36195 |

6.2.2 Example 2

Nickel-Mediated In Vivo Transfection

An experiment was conducted to determine if nickel promotes in vivo transfection. To perform this study, DNA/nickel mixtures were prepared by sequentially adding an appropriate amount of water, nickel chloride, and pCMV.FOX.Luc.2 plasmid DNA to a polystyrene tube with mixing. Mixtures were prepared at 0.3 mM and 0.9 mM nickel chloride and screened for in vivo transfection activity by administering 50 µl of the mixture, containing 32 µg DNA, to the right and left submandibular gland of male Sprague-Dawley rats. For comparison, 50 µl of a DNA/zinc mixture (0.9 mM zinc chloride, and 32 µg DNA) was also administered to the submandibular glands of rats. At 48 hours post administration, the glands were harvested and assayed for luciferase specific activity as described above. The average results obtained from eight individual glands are presented in Table 2. The results from this study demonstrate that nickel promotes in vivo transfection in a dose dependent manner. In addition, nickels ability to promote transfection is similar to that observed by using zinc.

TABLE 2

Comparison of $NiCl_2$— and $ZnCl_2$—Mediated In Vivo Transfection

| Metal Chloride[†] | Concentration [mM][‡] | Average[§] |
|---|---|---|
| Ni | 0.3 | 18391 |
| Ni | 0.9 | 65121 |
| Zn | 0.9 | 63842 |

[†]Metal Chloride present in nucleic acid/transition metal enhancer solution
[‡]Concentration of metal chloride used in nucleic acid/transition metal enhancer solution
[§]Average relative light units from eight rat submandibular glands

6.2.3 Example 3

Copper-Mediated In Vivo Transfection

An experiment was conducted to determine if copper promotes in vivo transfection. To perform this study, DNA/copper mixtures were prepared by sequentially adding an appropriate amount of water, Tris-HCl, EDTA, cuprous chloride, and DNA (pCMV.FOX.Luc.2) to a polystyrene tube. Mixtures were prepared at 0.3 mM, 0.9 mM, and 1.2 mM cuprous chloride and screened for in vivo transfection activity by administering 50 µl of a particular mixture, containing 32 µg DNA, to the right and left submandibular gland of four male Sprague-Dawley rats. For comparison, 50 µl of a DNA/zinc mixture (0.9 mM zinc chloride, and 32 µg DNA) was also administered to the submandibular glands of four rats. At 48 hours post administration, the glands were harvested and assayed for luciferase specific activity as described above. The average result obtained from each treatment condition examined in this study is presented in Table 3. The results demonstrate that copper can also be used to promote in vivo transfection. In addition, coppers ability to promote transfection is superior to that observed by using zinc.

TABLE 3

Comparison of $CuCl_2$— and $ZnCl_2$—Mediated In Vivo Transfection

| Metal Chloride[†] | Concentration [mM][‡] | Average[§] |
|---|---|---|
| Cu | 0.6 | 17667 |
| Cu | 0.9 | 42204 |
| Cu | 1.2 | 17194 |
| Zn | 0.9 | 5685 |

[†]Metal Chloride present in nucleic acid/transition metal enhancer solution
[‡]Concentration of metal chloride used in nucleic acid/transition metal enhancer solution
[§]Average relative light units from eight rat submandibular glands

6.2.4 Example 4

Cobalt-Mediated In Vivo Transfection

An experiment was conducted to determine if cobalt promotes in vivo transfection. To perform this study, DNA/cobalt mixtures were prepared by sequentially adding an appropriate amount of water, cobalt chloride, and DNA (pCMV.FOX.Luc.2) to a polystyrene tube. Mixtures were prepared at 0.3 mM and 0.9 mM cobalt chloride and screened for in vivo transfection activity by administering 50 µl of a particular mixture, containing 32 µg DNA, to the right and left submandibular gland of four male Sprague-Dawley rats. For comparison, 50 µl of a "free" DNA solution (32 µg DNA) was also administered to the submandibular glands of four rats. At 48 hours post administration, the glands were harvested and assayed for luciferase specific activity as described above. The average result obtained from each treatment condition examined in this study is presented in Table 4. The results from this study demonstrate that cobalt promotes in vivo transfection when compared to a "free" DNA solution. In addition, the observed improvement in transfection activity was observed at both of the cobalts concentrations screened.

TABLE 4

Effect of $CoCl_2$ on In Vivo Transfection[§]

| [$CoCl_2$] (mM) | Average |
|---|---|
| — | 23698 |
| 0.3 | 37219 |
| 0.9 | 44926 |

[§17] Data in each trial represent relative light units produced during the luciferase assay.

6.2.5 Example 5

Transition Metal-Mediated Transfection of the Mouse Lung

An experiment was conducted to determine if transition metals promote in vivo transfection of the mouse lung. To perform this study, a DNA/zinc mixture was prepared by sequentially adding an appropriate amount of water, zinc chloride, and DNA (pCMV.FOX.Luc.2) to a polystyrene tube. The final zinc chloride concentration of this mixture was 3.6 mM. The mixtures was screened for in vivo transfection activity by administering 150 µl of the mixture, containing 384 µg DNA, intratracheally to lungs of four male BALB/c mice as described above. For comparison, 150 µl of a DNA solution (354 µg DNA) was also administered to intratracheally to the lungs of four mice. At 48 hours post administration, the tracheal/lung block was dissected and assayed for luciferase specific activity as described above. The average result obtained from each treatment condition examined in this study is presented in Table 5. The results from this study demonstrate that transition metals can be used to promote in vivo transfection of the mouse lung. In this particular case, zinc chloride improves observed transfection activity by 5-fold relative to the "free" DNA solution.

TABLE 5

Effect of $ZnCl_2$ on Transfection of the Mouse Lung[§]

| Treatment Condition | Average |
|---|---|
| "free" DNA | 535.2 |
| DNA + $ZnCl_2$ | 2715.8 |

[§17] Data in each trial represent relative light units produced during the luciferase assay.

6.2.6 Example 6

Influence of Metal Ligand Substitution on Transition Metal-Mediated Transfection An experiment was conducted to determine if transition metal compounds other than transition metal chlorides have the ability to promote in vivo transfection. In this study, zinc chloride was compared to zinc sulfate and zinc acetate for the ability to enhance transfection of the rat salivary gland. For each zinc-containing compound, DNA/zinc mixtures were prepared by sequentially adding an appropriate amount of water; the zinc containing compound, either zinc chloride, zinc acetate, or zinc sulfate; and DNA (pCMV.FOX.Luc.2) to a polystyrene tube. The final zinc concentration of each mixture was 3.6 mM. The relative transfection activity of each zinc compound was determined by administering 50 µl of the DNA/zinc mixture (containing 128 µg DNA) into the right and left submandibular gland of male Sprague-Dawley rats. At 48 hours post administration, the glands were harvested and assayed for luciferase specific activity as described above. The average result obtained from each treatment condition examined in this study is presented in Table 6. The results demonstrate that zinc sulfate and zinc acetate are better than zinc chloride at promoting in vivo transfection. The study also demonstrates that transition metal compounds containing either organic ligands (acetate) or inorganic ligands (sulfate and chloride) are capable of promoting in vivo transfection.

TABLE 6

Effect of Zinc Ligand Structure on Observed Transfection Activity in the Rat Saliva Gland[§]

| TransitionMetal Enhancer | Average |
|---|---|
| $Zn(CH_3CO_2)_2$ | 309965 |
| $ZnCl_2$ | 243362 |
| $ZnSO_4$ | 355676 |

[§17] Data in each trial represent relative light units produced during the luciferase assay.

6.2.7 Example 7

Influence of pH on Transition Metal-Mediated Transfection

An experiment was conducted to determine the effect pH has on transition metal-mediated in vivo transfection. DNA/zinc mixtures containing 3.6 mM zinc chloride were prepared at pH 5.5, 6.5, 7.5 and 8.5. The relative transfection activity of these DNA/zinc mixtures was determined by administering 50 μl of each DNA/zinc mixture (containing 128 μg DNA) into the right and left submandibular glands of male Sprague-Dawley rats. For comparison, four rats received injections of a "free DNA" solution (50 μl, 128 μg, pH 7.5). At 48 hours post administration, the glands were harvested and assayed for luciferase specific activity as described above. The average result (n=4) obtained for each treatment condition examined in this study is presented in Table 7. The results demonstrate that, for the solutions screened, the pH of the zinc/DNA solution has a negligible effect on observed transfection activity.

TABLE 7

Effect of pH on $ZnCl_2$-Mediated Transfection of the Rat Salivay Gland[§]

| [ZnCl2] (mM) | pH | Average |
|---|---|---|
| 3.6 | 5.5 | 252446 |
| 3.6 | 6.5 | 196002 |
| — | 7.5 | 52397 |
| 3.6 | 7.5 | 260340 |
| 3.6 | 8.5 | 277958 |

[§17] Data in each trial represent relative light units produced during the luciferase assay.

6.2.8 Example 8

Influence of Media Composition on Transition Metal-Mediated Transfection

An experiment was conducted to determine if Tris-HCl and EDTA are essential components for an active nucleic acid/transition metal enhancer mixture. Tris-HCl and EDTA are commonly used as preservatives for DNA solutions. Tris-HCl and EDTA, collectively referred to as TE, inhibit DNase activity therefore preventing enzymatic degradation of DNA solutions. EDTA binds to calcium and magnesium ions, which are required for DNase activity. EDTA is also known to have an affinity for zinc and other transition metals. Since all the experiments mentioned above used nucleic acid/transition metal enhancer mixtures containing Tris-HCl and EDTA, the influence of these additives was studied. A test set of nucleic acid/transition metal enhancer mixtures, C-1 thru C-4, were prepared each differing in the concentrations of EDTA and Tris-HCl contained within them (See Table 8 for the composition of each solution). A set of control mixtures, D-1 thru D-4, corresponding to solutions C-1 thru C-4, was also prepared (See Table 8 for the composition of each solution). The control set of mixtures, D-1 thru D-4, were identical to the test mixtures, C-1 thru C-4, except that no zinc chloride was present in the control set. These mixtures were screened for transfection activity using the rat salivary gland model. At 48 hours post administration, the glands were harvested and assayed for luciferase specific activity as described above. The average result (n=4) obtained from each treatment condition examined in this study is presented in Table 8. The results of this study indicate that Tris-HCl and EDTA are not important components for an active DNA/zinc transfection mixture. However, DNA/zinc mixtures containing Tris-HCl and EDTA are more active than a "free" DNA solution (Table 1). Results obtained from this experiment suggest that "active" DNA/zinc mixtures may be prepared using many different formulation conditions.

TABLE 8

Influence of Transfection Media Composition on $ZnCl_2$—Mediated Transfection[§]

| Solution | [$ZnCl_2$] (mM) | [Tris-HCl] (mM) | [EDTA] (mM) | Relative Light Units |
|---|---|---|---|---|
| C-1 | 3.6 | 10 | 1 | 437597 |
| C-2 | 3.6 | 10 | 0 | 139291 |
| C-3 | 3.6 | 0 | 1 | 414083 |
| C-4 | 3.6 | 0 | 0 | 1354218 |
| D-1 | 0 | 10 | 1 | 26145 |
| D-2 | 0 | 10 | 0 | 30790 |
| D-3 | 0 | 0 | 1 | 38999 |
| D-4 | 0 | 0 | 0 | 42413 |

[§]Data in each trial represents relative light units produced during the luciferase assay.

6.2.9 Example 9

Zinc-Mediated Transfection of Rat Salivary Gland with Alpha-1 Antitrypsin.

An experiment was conducted to determine if transition metal-mediated transfection could be used to introduce an alpha-1 antitrypsin gene into the cells of the rat salivary gland. Alpha-1 antitrypsin is a secreted protein found in blood. In order to perform this study, a plasmid DNA containing the alpha-1 antitrypsin gene was prepared using procedures similar to those used to prepare the luciferase plasmid. A DNA/zinc mixture was prepared by sequentially adding an appropriate amount of water, zinc chloride, and DNA (pBAT-iMG-2) to a polystyrene tube. Aliquots of this mixture, 50 μl containing 128 mg DNA, were then injected into both the right and left submandibular glands of four rats. For comparison, 50 ml of a "free" DNA solution (128 mg DNA) were also administered to the submandibular glands of four rats. At 48 hours post administration, the glands were harvested, homogenized in lysis buffer (100 mM $K_2PO_4$, pH 7.0, 1 mM dithiothreitol, and 1% Triton X-100), then assayed for the presence of alpha-1 antitrypsin using the method described above. The results listed in Table 9 show that administration of a DNA/zinc mixture leads to higher levels of alpha-1 antitrypsin expression than administration of a "free" DNA solution.

TABLE 9

Effect of $ZnCl_2$ on Observed a-1-anti-Trypsin Expression in the Rat Salivary Gland

| [$ZnCl_2$] | α-1-AT Expression (mg/mL) |
|---|---|
| — | 19.4 |
| 3.6 | 31.6 |

6.2.10 Example 10

Effect of $ZnCl_2$ on Observed Luciferase Expression in the Rat Pancreas

Experiments were performed to determine the effect of $ZnCl_2$ on luciferase expression using the rat pancreas model described in section 6.1.7. Using the luciferase assay as described above, the relative effectiveness of pCMV.FOX.Luc-2 (i) in the absence of $ZnCl_2$ and (ii) in the presence of $ZnCl_2$ were each tested in independent trials. In each trial, 64 μg of pCMV.FOX.Luc-2 in a total volume of 100 μL was injected into the bile duct near the duodenum as described in section 6.1.7. In trials conducted in the presence of $ZnCl_2$, the concentration of $ZnCl_2$ in the injected solution was 1.8 mM. Luciferase activity was assayed after 48 hours of treatment. The average luciferase activity from the four trials conducted in the absence of $ZnCl_2$ was 7274 relative luciferase light units per 10 mg of pancreatic tissue. In contrast, the average luciferase activity from the four trials in which $ZnCl_2$ was 22028 relative luciferase light units per 10 mg of pancreatic tissue. The experiments demonstrate that the presence of $ZnCl_2$ significantly enhanced luciferase expression in the rat pancreas.

6.2.11 Example 11

Figure 3:
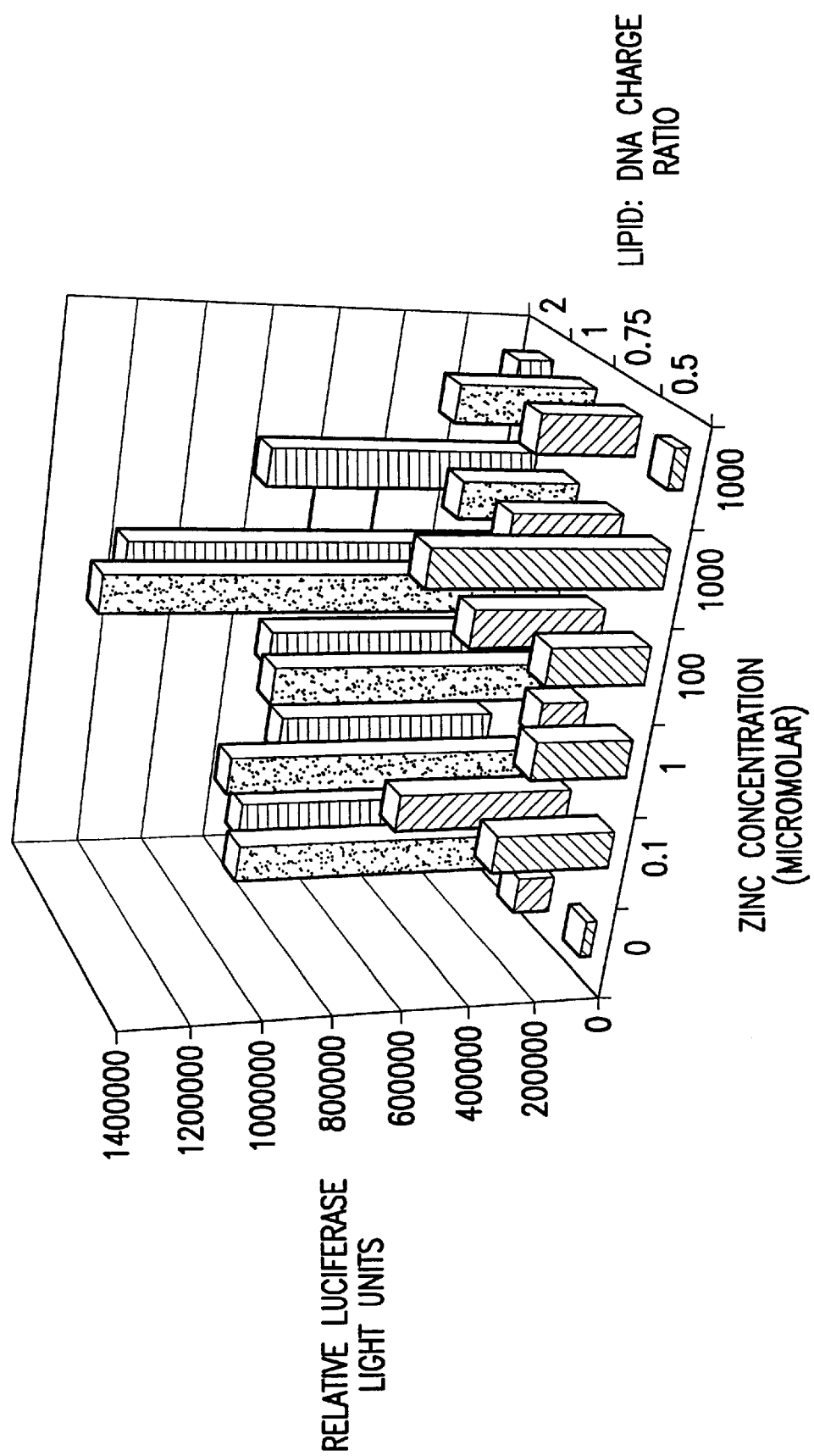
FIG. 3 is a chart showing the results of an experiment in which cationic lipid/pCMV.FOX.Luc.2 complexes at various charge ratios were screened for transfection activity in NIH 3T3 cells in the presence of various concentrations of $ZnCl_2$.

Effect of Added Zinc on Cationic Liposome-Mediated Gene Delivery to NIH 3T3 Cells An experiment was performed to demonstrate that $ZnCl_2$ can be used to enhance the in vitro transfection activity of cationic lipid/nucleic acid complexes. To perform this study, cationic lipid/nucleic acid/zinc mixtures were prepared by mixing appropriate amounts of serum-free DMEM, cationic liposomes, zinc chloride and pCMV.FOX.Luc.2 plasmid DNA in a polystyrene tube. In this experiment, the cationic lipid/nucleic acid complexes were formed at different cationic lipid:nucleic acid phosphate charge ratios. Specifically, complexes were formed at charge ratios of 0.5, 0.75, 1.0, and 2.0. Complexes formed at charge ratios above 1.0 possess a net positive charge whereas those with a charge ratio below 1.0 have a net negative charge. The cationic lipid/nucleic acid phosphate charge ratio is an important experimental parameter that influences the transfection activity of cationic lipid/nucleic acid complexes. In many instances, complexes possessing a net positive charge are more active than those with a net neutral or net negative charge. Cationic lipid/nucleic acid complexes at each charge ratio were screened for transfection activity in NIH 3T3 cells in the presence of different concentrations of zinc chloride (0.0, 0.1, 1, 10, 100, and 1000 μM). NIH 3T3 cells are a murine fibroblast tissue culture cell line commonly used to demonstrate the in vitro transfection activity of gene delivery reagents. After 48 hours post-application of the cationic lipid/DNA/zinc solutions to the cells, the cells were lysed with lysis buffer and the lysate was assayed for luciferase specific activity. As illustrated in FIG. 3 and Table 10, the data clearly illustrates that zinc, when added to a cationic liposome/DNA mixture, can enhance in vitro transfection of cultured NIH 3T3 murine fibroblast cells by two to forty fold depending on the cationic lipid to nucleic acid charge ratio. The effect was more pronounced at lower charge ratios, however, and effect was observed at all the charge ratios screened. The ability of the methods of the present invention to increase the activity of low charge ratio cationic lipid/DNA complexes is highly advantageous over prior art systems because highly charged complexes have a significant amount of associated cytotoxicity.

TABLE 10

Effect of Added Zinc on Cationic Liposome-Mediated Gene Delivery to NIH 3T3 Cells

| Lipid/DNA Charge Ratio | Zinc Concentration (μM) | | | | | |
|---|---|---|---|---|---|---|
| | 0 | 0.1 | 1 | 10 | 100 | 1000 |
| 0.5 | 34366.5 | 357320 | 289649.8 | 296498.3 | 690512.3 | 44053.75 |
| 0.75 | 113887 | 528118.8 | 141950 | 397689.3 | 334007.5 | 298625.5 |
| 1 | 869865 | 931446.8 | 835699.8 | 1366067 | 359188.5 | 414392 |
| 2 | 767710 | 677663.5 | 747069.5 | 1215879 | 827479.8 | 109543.8 |

| $ZnCl_2$ (μM) | Trial 1 | Trial 2 | Trial 3 | Trial 4 | Average |
|---|---|---|---|---|---|
| 0.5 Charge Ratio | | | | | |
| 0 | 3146 | 61387 | 21468 | 51465 | 34366.5 |
| 0.1 | 487868 | 426369 | 256897 | 258146 | 357320 |
| 1 | 385049 | 200471 | 304108 | 268971 | 289649.8 |
| 10 | 325001 | 323001 | 250110 | 287881 | 296498.3 |
| 100 | 351939 | 252969 | 294018 | 1863123 | 690512.3 |

TABLE 10-continued

Effect of Added Zinc on Cationic Liposome-Mediated Gene Delivery to NIH 3T3 Cells

| 1000 | 43835 | 40236 | 59395 | 32749 | 44053.75 |

0.75 Charge Ratio

| 0 | 118667 | 128866 | 103034 | 104981 | 113887 |
| 0.1 | 613179 | 556656 | 437658 | 504982 | 528118.8 |
| 1 | 127339 | 236302 | 123913 | 80246 | 141950 |
| 10 | 455299 | 465986 | 362168 | 307304 | 397689.3 |
| 100 | 404983 | 351094 | 358591 | 221362 | 334007.5 |
| 1000 | 335343 | 257292 | 374511 | 227356 | 298625.5 |

1 Charge Ratio

| 0 | 617205 | 876229 | 1077503 | 908523 | 869865 |
| 0.1 | 901184 | 862221 | 1113520 | 848862 | 931446.8 |
| 1 | 942667 | 864670 | 799992 | 735470 | 835699.8 |
| 10 | 2145687 | 1433861 | 1202748 | 681970 | 1366067 |
| 100 | 262768 | 379927 | 447492 | 346567 | 359188.5 |
| 1000 | 437998 | 443459 | 502263 | 273848 | 414392 |

2 Charge Ratio

| 0 | 1017767 | 777548 | 684552 | 590973 | 767710 |
| 0.1 | 596911 | 685311 | 818392 | 610040 | 677663.5 |
| 1 | 661803 | 814409 | 754168 | 757898 | 747069.5 |
| 10 | 1498720 | 1238992 | 1207690 | 918114 | 1215879 |
| 100 | 768327 | 880621 | 941720 | 719251 | 827479.8 |
| 1000 | 199493 | 48657 | 189902 | 123 | 109543.8 |

6.2.12 Example 12

Effect of Added Zinc on Cationic Liposome-Mediated Gene Delivery to Rat Submandibular Gland An experiment was performed to demonstrate that zinc chloride can be used to enhance the in vivo transfection activity of cationic lipid/nucleic acid complexes. To perform this study, cationic lipid/nucleic acid/zinc mixtures were prepared by mixing the appropriate amount of sterile water, cationic liposomes, zinc chloride and pCMV.FOX.hGH plasmid DNA in a polystyrene tube. Specifically, 40 microliters of a 3 mM 3:1 DOHBD:DOPE liposome mixture, 270 microliters of a 8.08 microgram/microliter pCMV.FOX.hGH plasmid DNA mixture, and an appropriate amount of a 70 mM zinc chloride mixture were added to a polystyrene tube containing a sufficient amount of water to give a final total volume of 2500 microliters. In this experiment, the final zinc chloride concentration was either 0.125 mM, 0.250 mM, or no zinc at all. The cationic lipid:DNA phosphate ratio in this study remained constant for all mixtures screened. Once prepared, 200 microliters of each mixture was instilled into the right and left submandibular glands of four male Sprague-Dawley rats. Thus, 175 micrograms of the plasmid DNA was instilled into each gland. After one week post-administration of the cationic lipid/nucleic acid/zinc mixtures, the salivary gland of the rats were extracted, mixed with a phosphate lysis buffer (10 mM, pH 8.0) and homogenized. The homogenate was then assayed for human growth hormone protein expression. The data (Table 11) illustrates that zinc, when added to a cationic liposome/nucleic acid mixture, can enhance in vivo transfection of the rat submandibular gland by at least two fold when compared to a cationic liposome/nucleic acid mixture not containing zinc.

TABLE 11

Effect of Added Zinc on Cationic Liposome-Mediated Gene Delivery to Rat Submandibular Gland

| [Zn] mM | Trial 1 | Trial 2 | Trial 3 | Trial 4 | Trial 5 | Trial 6 | Trial 7 | Trial 8 |
|---|---|---|---|---|---|---|---|---|
| 0 | 292.9 | 287.9 | 285.2 | 255.2 | 128.6 | 86.4 | 335.6 | 277.5 |
| 0.125 | 452.1 | 360.8 | 261.7 | 355.7 | 517.2 | 575.6 | 943.5 | 1084 |
| 0.25 | 857.731 | 753.3 | 272.6 | 315.3 | 604.3 | 449.9 | | |

| [Zn] mM | Average | Standard Deviation |
|---|---|---|
| 0 | 216.5889 | 87.67482 |
| 0.125 | 505.6361 | 294.0226 |
| 0.25 | 464.7687 | 236.9247 |

References Cited

All references cited are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. For example, it is to be understood that the invention is not limited to the particular methodology, protocols, cell types, tissues, vectors and reagents described because they may, of course, vary. It is also to be understood that the terminology used herein is for the purpose of describing particular embodiments only, and is not intended to limit the scope of the present invention. The specific embodiments described herein are offered by way of example only, and the invention is to be limited only by the terms of the appended claims, along with the full scope of equivalents to which such claims are entitled.

We claim:

1. A method for delivering a DNA into a cell of a mammal, said DNA encoding a peptide or protein operably linked to a promoter, the method comprising administering to said cell of said mammal a solution comprising an ionizable or ionized transition metal enhancer and said DNA, wherein said solution further comprises a cationic lipid.

2. The method of claim 1, wherein said cell is a secretory gland cell of said mammal.

3. The method of claim 2, wherein the secretory gland cell is selected from the group consisting of a salivary gland cell, a pancreatic cell, a mammary gland cell, a thyroid cell, a thymus cell, a pituitary gland cell, and a liver cell.

4. The method of claim 3, wherein the secretory gland cell is a salivary gland cell.

5. The method of claim 2, wherein said peptide or protein is secreted or released from said secretory gland cell.

6. The method of claim 2, wherein the peptide or protein is not secreted or released from the secretory gland cell.

7. The method of claim 1, wherein said DNA encoding said peptide or protein is expressed in a lung cell or a liver cell of said mammal.

8. The method of claim 7, wherein said DNA encoding said peptide or protein is expressed in a lung cell of said mammal.

9. The method of claim 1, wherein said solution is delivered to said mammal by intraductal delivery or direct administration.

10. The method of claim 1, wherein the solution is a buffered solution having a pH of about 4.0 to about 9.0.

11. The method of claim 10, wherein the solution has a pH of about 5.5 to about 8.5.

12. The method of claim 1, wherein the solution has a total salt concentration of less than about 250 micromolar.

13. The method of claim 1, wherein the solution has a cumulative salt concentration of less than about 50 micromolar.

14. The method of claim 1, wherein about 1 microgram to about 100 milligrams of the DNA is administered to said mammal.

15. The method of claim 1, wherein about 30 micrograms to about 30 milligrams of the DNA is administered to said mammal.

16. The method of claim 1, wherein a molar ratio of the ionizable or ionized transition metal enhancer to DNA in the solution is about 0.0001:1 to about 1:0.0001.

17. The method of claim 1, wherein the ionizable or ionized transition metal enhancer is a complex, adduct, cluster or salt of an element selected from the group consisting of a d-block element, a first row $f$-block element, aluminum, and gallium.

18. The method of claim 17, wherein the ionizable or ionized transition metal enhancer is a complex, adduct, cluster or salt of an element selected from the group consisting of zinc, nickel, cobalt, copper, aluminum, and gallium.

19. The method of claim 18, wherein the ionizable or ionized transition metal enhancer is selected from the group consisting of zinc sulfate, zinc acetate, nickel sulfate, nickel acetate, cobalt sulfate, cobalt acetate, copper sulfate, and copper acetate.

20. The method of claim 19, wherein the ionizable or ionized transition metal enhancer is zinc acetate or zinc sulfate.

21. The method of claim 1, wherein the ionizable or ionized transition metal enhancer is about 0.01 millimolar zinc sulfate to about 250 millimolar zinc sulfate in said solution.

22. The method of claim 21, wherein the ionizable or ionized transition metal enhancer is about 0.03 millimolar zinc sulfate to about 6.0 millimolar zinc sulfate in said solution.

23. The method of claim 1, wherein the ionizable or ionized transition metal enhancer is about 0.01 millimolar zinc acetate to about 250 millimolar zinc acetate in said solution.

24. The method of claim 1, wherein the ionizable or ionized transition metal enhancer is about 0.03 millimolar zinc acetate to about 6.0 millimolar zinc acetate in said solution.

25. The method of claim 1, wherein the ionizable or ionized transition metal enhancer is selected from the group consisting of zinc halide, nickel halide, cobalt halide, copper halide, aluminum halide, and gallium halide.

26. The method of claim 25, wherein the ionizable or ionized transition metal enhancer is selected from the group consisting of $ZnCl_2$, $NiCl_2$, $CoCl_2$, $CuCl_2$, $AlCl_2$, and $GaCl_2$.

27. The method of claim 1, wherein the ionizable or ionized transition metal enhancer is about 0.01 millimolar $ZnCl_2$ to about 250 millimolar $ZnCl_2$ in said solution.

28. The method of claim 1, wherein the ionizable or ionized transition metal enhancer is about 0.03 millimolar $ZnCl_2$ to about 6.0 millimolar $ZnCl_2$ in said solution.

29. The method of claim 1, wherein the ionizable or ionized transition metal enhancer is about 0.01 millimolar $NiCl_2$ to about 250 millimolar $NiCl_2$ in said solution.

30. The method of claim 29, wherein the ionizable or ionized transition metal enhancer is about 0.03 millimolar $NiCl_2$ to about 6.0 millimolar $NiCl_2$ in said solution.

31. The method of claim 1, wherein the ionizable or ionized transition metal enhancer is about 0.01 millimolar $CoCl_2$ to about 250 millimolar $CoCl_2$ in said solution.

32. The method of claim 31, herein the ionizable or ionized transition metal enhancer is about 0.03 millimolar $CoCl_2$ to about 6.0 millimolar $CoCl_2$ in said solution.

33. The method of claim 1, wherein the ionizable or ionized transition metal enhancer is about 0.01 millimolar $CuCl_2$ to about 250 millimolar $CuCl_2$ in said solution.

34. The method of claim 33, wherein the ionizable or ionized transition metal enhancer is about 0.03 millimolar $CuCl_2$ to about 6.0 millimolar $CuCl_2$ in said solution.

35. The method of claim 1, wherein the ionizable or ionized transition metal enhancer is about 0.01 millimolar $AlCl_2$ to about 250 millimolar $AlCl_2$ in said solution.

36. The method of claim 35, wherein the ionizable or ionized transition metal enhancer is about 0.01 millimolar $AlCl_2$ to about 250 millimolar $AlCl_2$ in said solution.

37. The method of claim 1, wherein the DNA is a plasmid.

38. The method of claim 1, wherein said DNA leads to expression of said peptide or protein and wherein said protein is selected from the group consisting of human growth hormone, luciferase, and human alpha-1 antitrypsin.

39. A method of delivering a DNA into a mammalian pancreatic cell, a liver cell, a salivary gland cell or a lung cell, said DNA encoding a peptide or protein operably linked to a promoter, the method comprising administering to said cell of said mammal a solution comprising said DNA and an ionizable or ionized transition metal enhancer selected from the group consisting of zinc chloride, copper chloride, nickel chloride, cobalt chloride, zinc sulfate, and zinc acetate.

40. The method of claim 1, wherein a cationic lipid:DNA phosphate charge ratio of said solution is about 0.01 to about 12.

41. The method of claim 1, wherein said cationic lipid is selected from the group consisting of 1:1 N,N-[bis(2-hydroxyethyl)]-N-methyl-N-[2,3-bis(tetradecanoyloxy)propyl]ammonium chloride and N,N,N'N'-tetramethyl-N,N'-bis(2-hydroxyethyl)-2,3-bis(9(z)-octadecenoyloxy)-1,4-butanediaminium iodide.

42. A method for in vitro transfection of a DNA into a cell, said DNA encoding a peptide or protein operably linked to a promoter, the method comprising administering to said cell of said mammal a solution comprising an ionizable or ionized transition metal enhancer, said DNA, and a cationic lipid.

43. The method of claim 42, wherein the cationic lipid/nucleic acid phosphate charge ratio of said solution is about 0.5 to about 2.0.

44. The method of claim 42, wherein the concentration of said ionizable or ionized transition metal enhancer in said solution is about 0.1 to about 1000 $\mu$M.

45. The method of claim 42, wherein the solution is formed by combining a molar ratio of cationic lipid to neutral lipid, said ionizable or ionized transition metal enhancer, and said DNA.

46. The method of claim 45, wherein said neutral lipid is dioleoylphosphatidylethanolamine.

47. The method of claim 42, wherein the ionizable or ionized transition metal enhancer is a complex, adduct, cluster or salt of an element selected from the group consisting of a d-block element, a first row $f$-block element, aluminum, and gallium.

48. The method of claim 42, wherein the ionizable or ionized transition metal enhancer is a complex, adduct, cluster or salt of an element selected from the group consisting of zinc, nickel, cobalt, copper, aluminum, and gallium.

49. The method of claim 42, wherein the ionizable or ionized transition metal enhancer is zinc chloride.

50. The method of claim 42, wherein said DNA leads to expression of said peptide or protein and said peptide or protein is luciferase.

51. The method of claim 42, wherein said cell is an NIH 3T3 cell.

* * * * *